(12) United States Patent
Peterson et al.

(10) Patent No.: US 11,020,494 B2
(45) Date of Patent: Jun. 1, 2021

(54) ANIMAL MODELS FOR NONALCOHOLIC FATTY LIVER DISEASE

(71) Applicant: CROWN BIOSCIENCE INC. (TAICANG), Taicang (CN)

(72) Inventors: Richard Peterson, Indianapolis, IN (US); Charles Van Jackson, Greenfield, IN (US); Gao Sun, Shanghai (CN); Guodong Zhang, Taicang (CN); Yixin (Jim) Wang, Lafayette, CA (US)

(73) Assignee: CROWN BIOSCIENCE INC. (TAICANG), Jiangsu (CN)

( * ) Notice: Subject to any disclaimer, the term of this patent is extended or adjusted under 35 U.S.C. 154(b) by 0 days.

(21) Appl. No.: 16/013,953

(22) Filed: Jun. 21, 2018

(65) Prior Publication Data
US 2018/0369423 A1 Dec. 27, 2018

Related U.S. Application Data

(60) Provisional application No. 62/523,755, filed on Jun. 22, 2017.

(51) Int. Cl.
*A61K 49/00* (2006.01)
*A01K 67/027* (2006.01)

(52) U.S. Cl.
CPC ........ *A61K 49/0008* (2013.01); *A01K 67/027* (2013.01); *A01K 2207/25* (2013.01); *A01K 2227/105* (2013.01); *A01K 2267/035* (2013.01); *A01K 2267/0362* (2013.01)

(58) Field of Classification Search
None
See application file for complete search history.

(56) References Cited

FOREIGN PATENT DOCUMENTS

JP 2005110632 A * 4/2005

OTHER PUBLICATIONS

Kanuri et al. In vitro and in vivo models of non-alcoholic fatty liver disease (NAFLD). 2013 Int. J. Mol. Sci. 14: 11963-11980. (Year: 2013).*
Hui et al. eLife 2015, 4:e05607 (Year: 2015).*
The Jackson Laboratory, description of Inbred strain AKR/J; (jax.org/strain/UrlAsPDF/00648) © 2021 The Jackson Laboratory.*

* cited by examiner

*Primary Examiner* — James D Schultz
(74) *Attorney, Agent, or Firm* — Jun He Law Offices P.O.; James J. Zhu

(57) ABSTRACT

The present disclosure provides non-human animal models of non-alcoholic fatty liver disease (NAFLD). Also provided are methods for producing the non-human animal models and uses of the non-human animal models to screen and evaluate agents for treating or preventing NAFLD.

8 Claims, 18 Drawing Sheets

ANIMAL MODELS FOR NONALCOHOLIC FATTY LIVER DISEASE

CROSS-REFERENCE TO RELATED APPLICATIONS

This application claims priority to U.S. provisional patent application no. 62/523,755, filed Jun. 22, 2017, the disclosure of which is incorporated herein by reference.

GRANT INFORMATION

This invention was made with Government support under SBIR Grant No. 2R44DK082065, awarded by the National Institute of Health. The Government has certain rights in this invention.

FIELD OF THE INVENTION

The present invention generally relates to animal models, the method making the same and the uses thereof In particular, the present invention relates to animal models for nonalcoholic fatty liver disease and for metabolic syndrome.

BACKGROUND

Non-alcoholic fatty liver disease (NAFLD) is a condition in which excess fat is stored in the liver of a person without excessive alcohol consumption. It is estimated that 25% of the world's general population meet the criteria for a diagnosis of NAFLD; NAFLD is more common in men and increases with age. The incidence of NAFLD also appears to be stratified across ethnic groups: Hispanics (45%)>Caucasians (33%)>African-Americans (24%).

The initial stage of NAFLD is characterized by the accumulation of ectopic fat in hepatocytes (steatosis). Steatosis is generally a benign, asymptomatic condition; however, with concurrent obesity/metabolic disturbances, steatosis can progress to non-alcoholic steatohepatitis (NASH) and in severe cases hepatocellular carcinoma (HCC) and liver failure. Histologically NASH is characterized by hepatocellular ballooning, inflammation and increased risk for liver fibrosis. Unlike benign steatosis, NASH represents a significant health threat that progresses to fibrosis/cirrhosis in 10-28% of patients. Further progression from NASH to fibrosis/cirrhosis is highly predictive of mortality in these patients.

The study of human NAFLD and its progression is hampered by the slow (decades) development of disease as well as tools available for staging the disease. The significant health threat ascribed to NASH versus the often-benign steatosis, makes early differentiation a necessary step in predicting which patients will progress to fibrosis and eventually liver failure. Currently, the staging of the fatty liver environment relies on histological evaluation from liver biopsy which is invasive, expensive and not practical for screening all NAFLD patients. While much research is ongoing to identify non-invasive tools for staging, biopsy remains the gold standard and reliable clinical biomarkers are not yet available. Thus, attempts have been made to develop rodent models of fatty liver disease to aid in the investigation of the pathophysiological and morphological findings characteristic of NAFLD, as well as histological characteristics such as steatosis, interlobular inflammation, hepatocellular ballooning, fibrosis and be susceptible to liver tumors seen in humans.

Over the last several years, investigators have taken different approaches to developing mouse models of NAFLD and NASH, including methionine-choline deficient diet (Machado M V et al. PLoS One.10(5):e0127991), high fat diets with and without fructose in C57BL/6J and ob/ob mice (Charlton M et al. Am J Physiol Gastrointest Liver Physiol. 301(5):G825-34; Itagaki H et al. Int J Clin Exp Pathol.6(12):2683-96; Kristiansen M N et al. World J Hepatol. 8(16):673-84; Tetri L H et al. Am J Physiol Gastrointest Liver Physiol. 295(5):G987-95) and the STAM model where 4 day old mice are given streptozotocin plus high fat diet (Jojima T et al. Diabetol Metab Syndr.8:45; Saito K et al. Sci Rep. 5:12466).

However, these animal models fail to accurately display the characteristic of NAFLD. For example, initial attention has been placed on producing fibrosis as quickly as possible with the methionine-choline deficient (MCD) diet. The mice on the MCD diet are not obese, actually loose significant body weight (30%), and are not insulin resistant or hyperlipidemic during disease progression. The STAM model is characterized by type 1 diabetes induced with streptozotocin, rather than type 2 diabetes on a high fat diet and produces fibrosis after 12 weeks on diet and eventually HCC. Therefore, there is a continuing need to develop new animal model for NAFLD.

SUMMARY OF INVENTION

In one aspect, the present disclosure provides a method for producing a non-human animal model of non-alcoholic fatty liver disease (NAFLD). In an embodiment, the method comprising obtaining a FATZO mouse at a young age and feeding the FATZO mouse with a diet of high-fat, high cholesterol and high fructose for a period of time.

In certain embodiments, the diet comprises fat of 40% kcal and 5% fructose in drinking water.

In certain embodiments, the NAFLD is steatosis, non-alcoholic steatohepatitis (NASH), cirrhosis or liver cancer.

In certain embodiments, the young age is about 6-12-week old (e.g., 6, 7, 8, 9, 10, 11 or 12 weeks old).

In certain embodiments, the period of time is about 4 weeks, 16 weeks or 20 weeks.

In a second aspect, the present disclosure provides a non-human animal model of NAFLD. In certain embodiments, the non-human animal model of NAFLD is produced by feeding a FATZO mouse of a young age with a diet of high-fat, high cholesterol and high fructose for a period of time.

In a third aspect, the present disclosure provides a method of screening for an agent for treating or preventing NAFLD. In one embodiment, the method comprises: (a) administering a candidate agent to the non-human animal model described herein; and (b) evaluating an ameliorative effect on the NAFLD.

In a fourth aspect, the present disclosure provides a method of evaluating a medicament for treating NAFLD. In one embodiment, the method comprises: (a) administering the medicament to the non-human animal model described herein; and (b) evaluating an ameliorative effect on the NAFLD.

In a fifth aspect, the present disclosure provides a method for producing a non-human animal model of diabetes complication. In one embodiment, the method comprises (a) obtaining a FATZO mouse of a young age; (b) determining that the FATZO mouse has a body weight within a body weight range; and (c) selecting the FATZO mouse for studying the diabetes complication.

In certain embodiments, the young age is about 6 weeks.

In certain embodiments, the diabetes complication is nephropathy, cardiomyopathy, vascular disease, retinopathy, or neuropathy.

In certain embodiments, the body weight range is 23-26.9 g. In certain embodiments, the body weight range is 27-29.9 g. In certain embodiments, wherein the body weight range is at least 30 g.

In a sixth aspect, the present disclosure provides a method of screening for an agent for treating or preventing diabetes or diabetes complications. In one embodiment, the method comprises: (a) administering a candidate agent to the non-human animal model described herein; and (b) evaluating an ameliorative effect on the diabetes or diabetes complications.

In a seventh aspect, the present disclosure provides a method of evaluating a medicament for treating diabetes or diabetes complication. In one embodiment, the method comprises: (a) administering the medicament to the non-human animal model described herein; and (b) evaluating an ameliorative effect on the diabetes or diabetes complications.

BRIEF DESCRIPTION OF THE DRAWINGS

The accompanying drawings, which are incorporated herein, form part of the specification. Together with this written description, the drawings further serve to explain the principles of, and to enable a person skilled in the relevant art(s), to make and use the present invention.

FIG. 1A shows the body weight in FATZO mice fed with CD or WDF for 20 weeks. FIG. 1B shows the body fat in FATZO mice fed with CD or WDF for 20 weeks. FIG. 1C shows the total cholesterol in FATZO mice fed with CD or WDF for 20 weeks. FIG. 1D shows the triglyceride in FATZO mice fed with CD or WDF for 20 weeks. FIG. 1E shows the ALT in FATZO mice fed with CD or WDF for 20 weeks. FIG. 1F shows the AST in FATZO mice fed with CD or WDF for 20 weeks. FIG. 1G shows the liver weight in FATZO mice fed with CD or WDF for 20 weeks. FIG. 1H shows the hepatic triglyceride content in FATZO mice fed with CD or WDF for 20 weeks. Data were presented as mean±SEM. *p<0.05, ***p<0.005 vs vehicle controls.

FIG. 3A shows the steatosis scores. FIG. 3B shows the hepatic ballooning scores. FIG. 3C shows the lobular inflammation scores. FIG. 3D shows the fibrosis scores. FIG. 3E shows the NAS scores. Data were presented as mean±SEM. *p<0.05, ***p<0.005 vs vehicle controls.

FIG. 4A shows the body weight in WDF fed FATZO mice treated with vehicle or OCA (30 mg/kg, QD). FIG. 4B shows the blood triglyceride in WDF fed FATZO mice treated with vehicle or OCA (30 mg/kg, QD). FIG. 4C shows the total cholesterol in WDF fed FATZO mice treated with vehicle or OCA (30 mg/kg, QD). FIG. 4D shows the LDL in WDF fed FATZO mice treated with vehicle or OCA (30 mg/kg, QD). FIG. 4E shows the ALT in WDF fed FATZO mice treated with vehicle or OCA (30 mg/kg, QD). FIG. 4F shows the AST in WDF fed FATZO mice treated with vehicle or OCA (30 mg/kg, QD). FIG. 4G shows the liver weight in WDF fed FATZO mice treated with vehicle or OCA (30 mg/kg, QD). FIG. 4H shows the hepatic triglyceride content in WDF fed FATZO mice treated with vehicle or OCA (30 mg/kg, QD). Data were presented as mean±SEM. *p<0.05 vs vehicle controls.

FIG. 6A shows the hepatic ballooning score. FIG. 6B shows the steatosis score. FIG. 6C shows the lobular inflammation score. FIG. 6D shows the fibrosis score. FIG. 6E shows the NAS score. Data were presented as mean±SEM. *p<0.05 vs vehicle controls.

DETAILED DESCRIPTION OF THE INVENTION

Figure 1A:
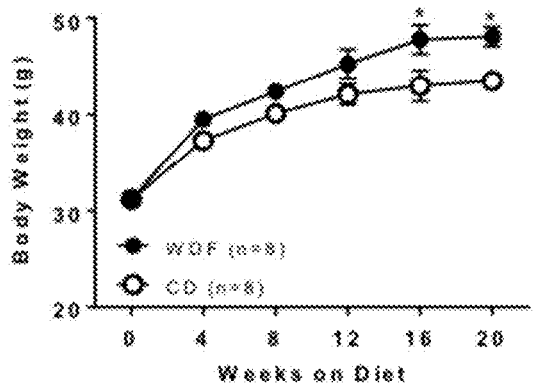
FIGS. 1A-1H shows Development of NAFLD/NASH in FATZO mice fed with CD or WDF diet.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definition

The following definitions are provided to assist the reader. Unless otherwise defined, all terms of art, notations and other scientific or medical terms or terminology used herein are intended to have the meanings commonly understood by those of skill in the art. In some cases, terms with commonly understood meanings are defined herein for clarity and/or for ready reference, and the inclusion of such definitions herein should not necessarily be construed to represent a substantial difference over the definition of the term as generally understood in the art.

As used herein, the singular forms "a", "an" and "the" include plural references unless the context clearly dictates otherwise.

As used herein, an "animal model" refers to a living organism with an inherited, naturally acquired, or induced pathological process that in one or more respects resembles the same phenomenon in a person.

It is noted that in this disclosure, terms such as "comprises", "comprised", "comprising", "contains", "containing" and the like have the meaning attributed in United States Patent law; they are inclusive or open-ended and do not exclude additional, un-recited elements or method steps. Terms such as "consisting essentially of" and "consists essentially of" have the meaning attributed in United States Patent law; they allow for the inclusion of additional ingredients or steps that do not materially affect the basic and novel characteristics of the claimed invention. The terms "consists of" and "consisting of" have the meaning ascribed to them in United States Patent law; namely that these terms are close ended.

As used herein, FATZO mouse refers a polygenic model developed by cross-breeding C57BL/6J mice with AKR/J mice and then selectively in-breeding for obesity, hyperglycemia and insulin resistance. This model is unique in that it possesses an intact leptin pathway, unlike the ob/ob or db/db mouse monogenic models of obesity and type 2 diabetes, thereby making it more translatable to the human disease.

As used herein, obeticholic acid (OCA) refers to a semi-synthetic bile acid that acts on the nuclear farnesoid X receptor (FXR) which is expressed predominantly in liver, kidney and intestine to regulate bile acid homeostasis, hepatic lipid metabolism as well as immune function. It was originally developed for the treatment of primary biliary cholangitis and is currently being tested for NASH in several clinical trials. OCA has shown effects of improvement in liver function and pathology in human and pre-clinical NASH models.

Animal Models of NAFLD

Non-alcoholic fatty liver disease (NAFLD) is an all-encompassing term used to describe the fatty liver environment in the absence of excessive alcohol consumption. It is estimated that 25% of the world's general population meet the criteria for a diagnosis of NAFLD; NAFLD is more common in men and increases with age. The incidence of NAFLD also appears to be stratified across ethnic groups: Hispanics (45%)>Caucasians (33%)>African-Americans (24%).

The initial stage of NAFLD is characterized by the accumulation of ectopic fat in hepatocytes (steatosis). Steatosis is generally a benign, asymptomatic condition; however, with concurrent obesity/metabolic disturbances, steatosis can progress to non-alcoholic steatohepatitis (NASH) and in severe cases hepatocellular carcinoma (HCC) and liver failure. Histologically NASH is characterized by hepatocellular ballooning, inflammation and increased risk for liver fibrosis. Unlike benign steatosis, NASH represents a significant health threat that progresses to fibrosis/cirrhosis in 10-28% of patients. Further progression from NASH to fibrosis/cirrhosis is highly predictive of mortality in these patients.

The study of human NAFLD and its progression is hampered by the slow (decades) development of disease as well as tools available for staging the disease. Therefore, an animal model accurately displays the characteristics of NAFLD is needed.

Therefore, the present disclosure in one aspect provides a method for producing a non-human animal model of non-alcoholic fatty liver disease (NAFLD). In an embodiment, the method comprising obtaining a FATZO mouse at a young age and feeding the FATZO mouse with a diet of high-fat, high cholesterol and high fructose for a period of time.

As used herein, a mouse is considered young from about 3 weeks to about 8 weeks old. In some embodiments, the young age as described herein is about 3 weeks, 4 weeks, 5 weeks, 6 weeks, 7 weeks or 8 weeks old.

As used herein, mouse diet refers to the sum of food consumed by a mouse, especially a mouse raised in a laboratory or facility. The ingredients and compositions of mouse diet are known in the art. For example, ingredients of a formulated lab mouse diet may include, without limitation, ground corn, ehulled soybean meal, whole wheat, fish meal, wheat middlings, porcine animal fat preserved with BHA and citric acid, cane molasses, porcine meat and bone meal, ground oats, wheat germ, brewers dried yeast, dehydrated alfalfa meal, dried beet pulp, whey, calcium carbonate, salt, menadione dimethylpyrimidinol bisulfite (source of vitamin K), choline chloride, cholecalciferol, DL-methionine, vitamin A acetate, pyridoxine hydrochloride, dl-alpha tocopheryl acetate (form of vitamin E), folic acid, thiamine mononitrate, nicotinic acid, calcium pantothenate, riboflavin supplement, vitamin B 12 supplement, manganous oxide, zinc oxide, ferrous carbonate, copper sulfate, zinc sulfate, calcium iodate, cobalt carbonate.

As used herein, a mouse diet of high-fat means a diet in which about 20-40% kcals (e.g., about 20%, 25%, 30%, 35%, 40%) are from fat.

In one example, a high-fat mouse diet has the formulation as listed in Table 1.

TABLE 1 formulation of high-fat mouse diet

| Class description | Ingredient | Grams |
| --- | --- | --- |
| Protein | Casein, Lactic, 30 Mesh | 195.0 g |
| Protein | Methionine, DL | 3.0 g |
| Carbohydrate | Sucrose, Fine Granulated | 350.0 g |
| Carbohydrate | Lodex 10 | 100.0 g |
| Carbohydrate | Starch, Corn | 50.0 g |
| Fiber | Solka Floc, FCC200 | 50.0 g |
| Fat | Butter, Anhydrous | 200.0 g |
| Fat | Corn Oil | 10.0 g |
| Mineral | S10001A | 17.5 g |
| Mineral | Calcium Phosphate, Dibasic | 17.5 g |

TABLE 1-continued formulation of high-fat mouse diet

| Class description | Ingredient | Grams |
|---|---|---|
| Mineral | Calcium Carbonate, Light, USP | 4.0 g |
| Vitamin | Choline Bitartrate | 2.0 g |
| Vitamin | V10001C | 1.0 g |
| Anti-oxidents | Ethoxyquin | 0.0 g |
| Special | Cholesterol, NF | 1.5 g |
| | Total: | 1001.5 g |

As used herein, a mouse diet of high-fructose means a diet which contains about 5-20% (e.g., about 5%, 10%, 15% or 20%) fructose, e.g., in drinking water.

In certain embodiments, the diet comprises fat of 40% kcal and 5% fructose in drinking water.

As used herein, feeding a mouse with a diet means the mouse is fed mainly with the diet, i.e., at least 80%, 85%, 90% of the food fed to the mouse is based on the diet.

In certain embodiments, the period of time is about 2 weeks, 3 weeks, 4 weeks, 5 weeks, 6 weeks, 7 weeks, 8 weeks, 9 weeks, 10 weeks, 12 weeks, 14 weeks, 16 weeks, 18 weeks, 20 weeks or more.

In one example, FATZO mice fed the WDF diet developed NAFLD and NASH with progressive steatosis and fibrosis with consistent ballooning and inflammation over 20 weeks when compared to FATZO mice fed regular CD. On gross necropsy, the livers from the mice fed the WDF diet were significantly larger and pale in color when compared to mice fed CD. In the plasma, increases in the liver enzymes, ALT and AST, and cholesterol were observed in the WDF diet fed animals as early as 4 weeks on diet and remained significantly higher compared to values obtained from animals on CD over the 20 weeks of observation. Plasma triglycerides were not elevated in the WDF diet fed animals when compared to the CD fed animals; as observed in the ob/ob NASH models. However, liver triglycerides were elevated at 12, 16 and 20 weeks in mice fed the WDF diet compared to mice fed CD (1.4-2.9 fold higher). The mice fed WDF had elevated glucose levels but did not become diabetic (>250 mg/dL) as compared to the mice fed CD; a common finding seen in the high fat/fructose fed C57BL/6 and ob/ob models. The FATZO mouse was equally hyperinsulinemic and insulin resistant in both WDF and CD fed groups.

On gross necropsy, the livers from WDF diet fed FATZO mice were pale in color and had significantly higher liver/% BW ratios when compared to their CD fed groups. Histologically, the livers from the FATZO mouse fed the WDF diet, demonstrated steatosis as early as 4 weeks on diet which progressed to steatohepatitis characterized by balloon degeneration, lobular inflammation and fibrosis. The composite NAS score in the FATZO mouse fed WDF was equivalent to "5" at 16 and 20 weeks on diet; indicative of "definitive"

NASH. Mild fibrosis was observed as early as 16 weeks on diet in 50% of the animals fed WDF and progressed to 100% of animals demonstrating moderate fibrosis scores of 1.5 at 20 weeks, respectively.

In a second aspect, the present disclosure provides a non-human animal model of NAFLD produced by the methods described herein. In certain embodiments, the non-human animal model of NAFLD is produced by feeding a FATZO mouse of a young age with a diet of high-fat and high fructose for a period of time.

Animal Models of Diabetes

The purpose of developing the FATZO mouse was to create a more translatable model for understanding the physiological and cellular mechanisms that lead to diabetes. One of the strengths of the model is the prolonged time during which animals are hyperglycemic without the loss of circulating insulin levels or decreases in pancreatic insulin content. Hyperinsulinemia concurrent with hyperglycemia, as biomarkers of insulin resistance, make this mouse a viable model to study mechanisms leading to increased insulin sensitivity.

The characteristics of the FATZO model give it several advantages over the commonly used models. The most frequently mentioned diabetic mouse models used in basic research and drug screening are those with leptin pathway defects (db/db and ob/ob) and the C57BL/6 DIO model. Since single-gene leptin pathway defects are very rare in the human population, animals with these defects are not representative of the clinical landscape. The ob/ob model on the C57BL/6J background, lacks active leptin. It has large islets which respond by releasing insulin with glucose elevations. This gene disruption on the C57BL/6J background has been characterized as a "model for the prediabetic state" with beta cell proliferation, hyperphagia, hyperinsulinemia, hyperglycemia, reduced metabolism and depressed thermoregulatory capacity. Since ob/ob mice do not exhibit beta cell failure and at older ages actually have reduced glucose levels they have limited usefulness as a model for testing antidiabetic compounds. The db/db mutation on the C57BL/Ks has a dysfunctional leptin receptor. This mutation on the Ks background results in obesity and a very early onset of hyperglycemia with beta cell failure. These characteristics result in a very severe model of diabetes and beta cell failure. The rapidity of beta cell failure in the db/db model limits its usefulness in studying drugs that modulate beta cell health and the effectiveness of native pancreatic insulin. In both the ob/ob and db/db models, defects in leptin signaling also interfere with the normal feedback mechanisms to the hypothalamus that are responsible for the control of body weight, feeding and energy expenditure. Thus these models are ineffective for testing compounds designed to modulate mechanisms mediated through the CNS. The DIO model, with intact leptin signaling, has been successfully used to demonstrate the effects of excessive caloric intake on obesity. Although the DIO model exhibits obesity, insulin resistance and glucose intolerance, modest glucose levels narrow the treatment window for testing the effects of anti-hyperglycemic compounds.

The FATZO mouse was developed by crossing two commonly used DIO models the C57BL/6 and the AKR/J followed by selective inbreeding to genetic homogeneity (30+generations). The selection of higher body weight animals for breeding was preferred to promote obesity; however, excessive body weight resulted in lower pregnancy rates, smaller liters and reduced survival of offspring. The result of this selection process was effective, but not optimal and has led to a significant variation in body weight of FATZO offspring when fed normal chow diet. This variation is apparent at weaning and carries through to adulthood. Independent of initial body weight, abnormal glucose disposal is apparent compared to control mice. Consequently, there is a need to develop improved methods for generating FATZO mouse model that consistently display characteristics of diabetes and diabetes complications.

Therefore, the present disclosure in another aspect provides a method for producing a non-human animal model of diabetes or diabetes complications. In one embodiment, the method comprises (a) obtaining a FATZO mouse of a young age; (b) determining that the FATZO mouse has a body weight within a body weight range; and (c) selecting the FATZO mouse for studying the diabetes or diabetes complications.

In certain embodiments, the young age is about 6 weeks.

In certain embodiments, the body weight range is 23-26.9 g. In certain embodiments, the body weight range is 27-29.9 g. In certain embodiments, wherein the body weight range is at least 30 g.

In certain embodiments, the diabetes complication is nephropathy, cardiomyopathy, vascular disease, retinopathy, or neuropathy.

In certain embodiments, the FATZO mouse is fed with a diet of high fat and high fructose.

In yet another aspect, the present disclosure provides a non-human animal model of diabetes or diabetes complications produced by the method described herein.

In another aspect, the present disclosure provides a non-human animal model of diabetes complications produced by the method described herein.

Use of the Animal Models

In another aspect, the present disclosure provides a method of screening for an agent for treating or preventing NAFLD. In one embodiment, the method comprises: (a) administering a candidate agent to the non-human animal model described herein; and (b) evaluating an ameliorative effect on the NAFLD.

In yet another aspect, the present disclosure provides a method of evaluating a medicament for treating NAFLD. In one embodiment, the method comprises: (a) administering the medicament to the non-human animal model of claim 4; and (b) evaluating an ameliorative effect on the NAFLD.

Multiple drugs have been in the development stage for the specific treatment of NASH. Among them, obeticholic acid (OCA), a semi-synthetic bile acid that acts on the nuclear farnesoid X receptor (FXR) is in the most advanced stage of clinical trial with evidence of significant alleviation of plasma liver ALT and AST levels and mild improvement in steatosis, hepatic ballooning, lobular inflammation and fibrosis. In pre-clinical rodent studies, OCA has shown benefits in reducing hepatic lipid accumulation, liver enzyme activities, steatosis and fibrosis, though the models and dosing regimen selected might largely affect the final manifest of the drug efficacy.

Figure 4A:
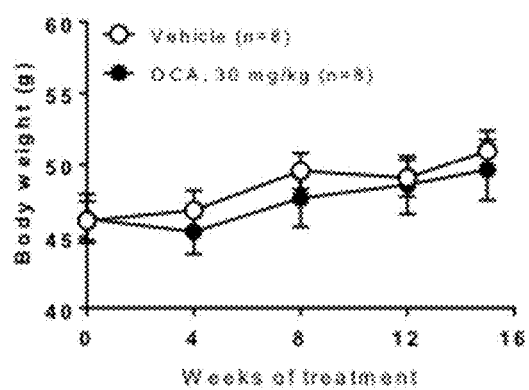
FIGS. 4A-4H show that OCA treatment improves liver function and lipid metabolism in FATZO mice fed WDF.
Figure 4B:
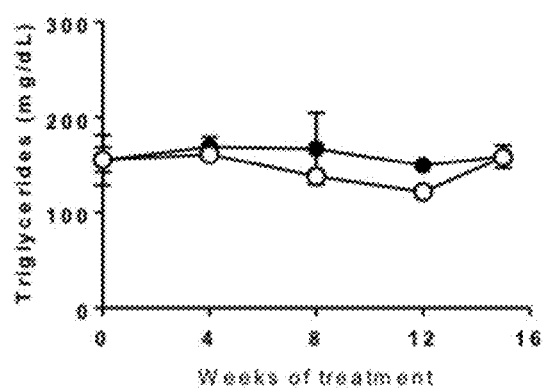
Figure 4C:
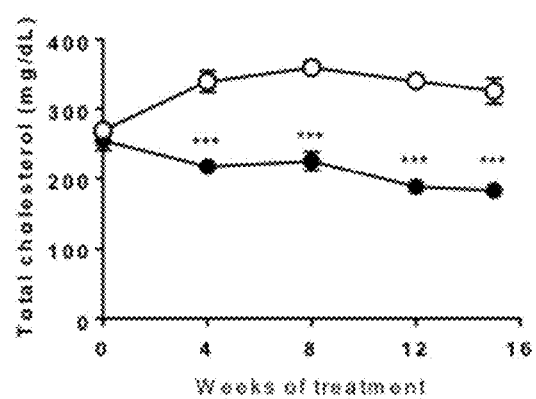
Figure 4D:
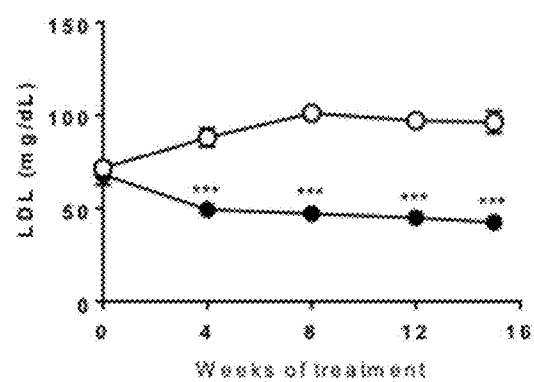
Figure 4E:
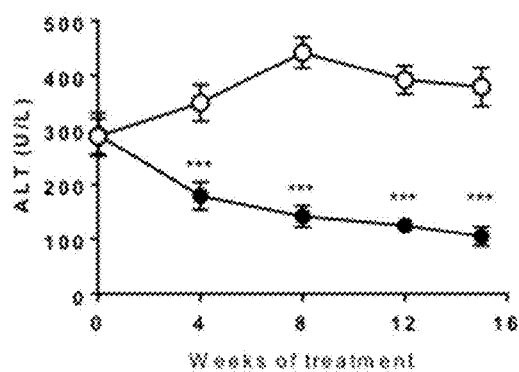
Figure 4F:
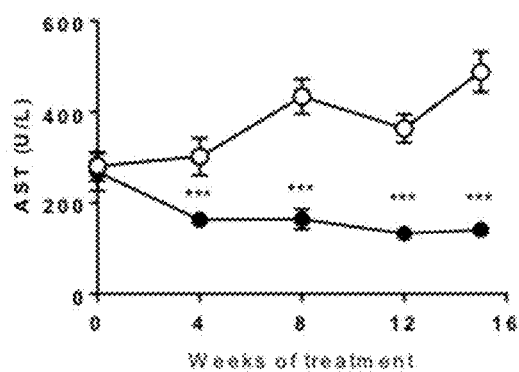
Figure 5:
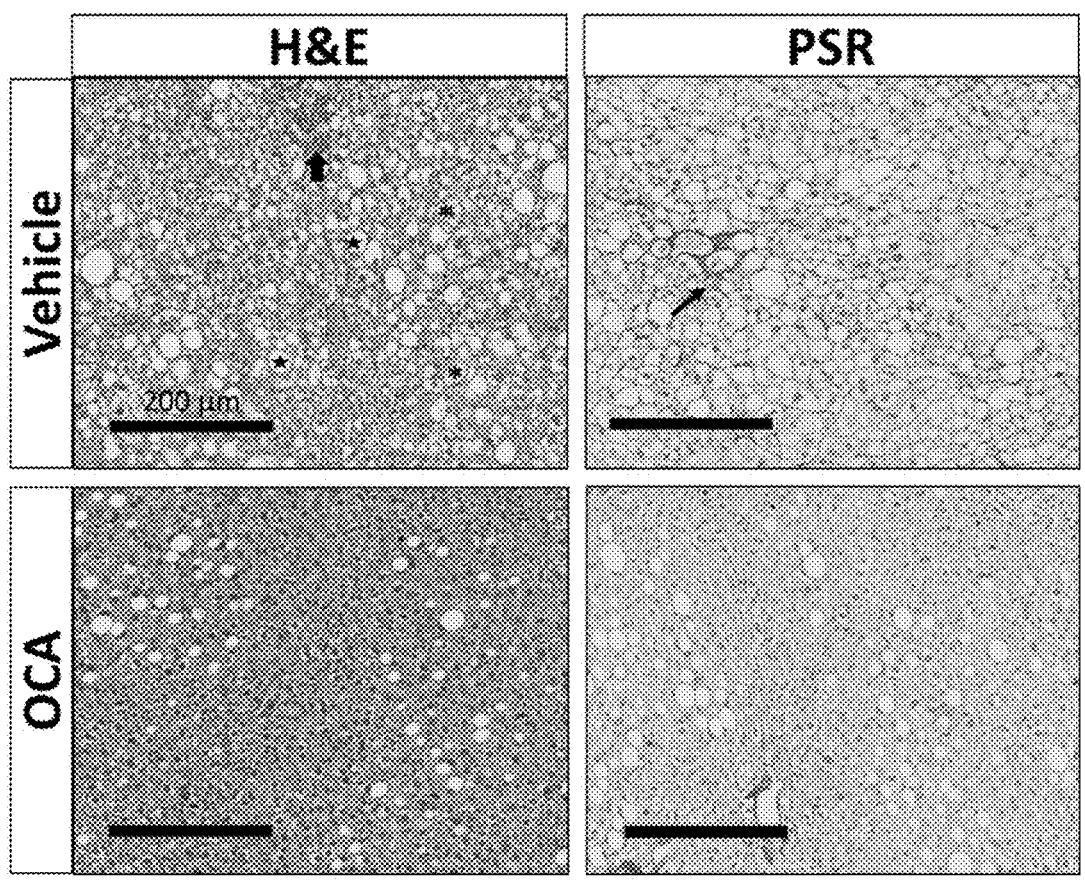
FIG. 5 shows that OCA treatment improves hepatic ballooning in NASH FATZO mice. Representative images of the H&E and Picro Sirius Red (PSR) staining of the livers removed from NAFLD/NASH FATZO mice treated with OCA or vehicle for 15 weeks.

In one example, FATZO mice fed WDF, OCA treatment for 15 weeks from 8 weeks on diet significantly brought down plasma ALT and AST levels almost to the values before WDF induction (FIGS. 4E and 4F). The results were reflective of what was seen in the treatment of NASH patients. In addition, OCA appeared to be more efficacious in reducing liver enzymes in FATZO fed WDF compared to ob/ob mice fed with AMLN diet with 8 weeks of treatment, where impacts of OCA on plasma liver enzymes in the latter model were minimal. Moreover, OCA treatment improved hepatic ballooning leading to overall reduction in NAS score and increased the numbers in animals with absence of fibrosis in WDF fed FATZO mice (FIGS. 5 and 6). The data suggested that FATZO mice fed with WDF diet can provide the NASH phenotypes in the time frame that is suitable for the anti-NASH drug intervention.

In another aspect, the present disclosure provides a method of screening for an agent for treating or preventing diabetes or diabetes complications. In one embodiment, the method comprises: (a) administering a candidate agent to the non-human animal model described herein; and (b) evaluating an ameliorative effect on the diabetes or diabetes complications.

In another aspect, the present disclosure provides a method of evaluating a medicament for treating diabetes or diabetes complication. In one embodiment, the method comprises: (a) administering the medicament to the non-human animal model described herein; and (b) evaluating an ameliorative effect on the diabetes or diabetes complications.

Metformin is accepted as a first line therapy in patients with type 2 diabetes and is the cornerstone of oral blood glucose lowering therapy. Metformin lowers fasting glucose and improves glucose tolerance in pre-diabetic as well as overtly diabetic individuals. Metformin effectively improves glucose disposal in high fat fed mice. As monotherapy in humans, a modest loss of body weight occurs in non-diabetic as well as obese diabetic patients. In addition, administration of metformin is associated with weight loss in obese DIO mice.

Rosiglitazone is a thiazolidinedione (TZD) insulin sensitizer, which has been shown to favorably influence pancreatic beta cell survival and function in rodent models of diabetes. Decreased insulin resistance and reduced hyperglycemia have been observed in humans and in obese mice following treatment with rosiglitazone. The major clinical side effect of rosiglitazone is significant weight gain.

The actions of glucagon-like peptide (GLP-1) on insulin release and an apparent impairment in the hormones actions in diabetic patients has led to the development of GLP-1 receptor agonists to improve glucose homeostasis in diabetic patients. In patients whose diabetes is not adequately controlled by metformin or a TZD, GLP-1 receptor agonists are often added to reach treatment goals. Ongoing efforts to maximize GLP-1 therapy have focused on lengthening the duration of action to decrease frequency of administration. Although semaglutide is a longer acting GLP-1 agonist and has demonstrated efficacy in humans when administered once weekly, it has a shortened period of effectiveness in rodents. Similar to other proteins such as gamma globulin and albumin, internal data have demonstrated that the half-life of semaglutide is significantly shorter in rodents than in man. Based on these internal data we selected dosing every 3 days. Other long acting GLP-1 based receptor agonists are now clinically available. The GLP-1 receptor agonists have also been shown to inhibit cumulative feed intake, reduce body weight and improve glucose tolerance in DIO mice.

In one example, it was shown that the obese, insulin resistant FATZO mouse responded to the three classes of anti-diabetic agents described above in a fashion comparable to that of humans and other obese models of type 2 diabetes. Body weight reduction with improved glucose tolerance was observed in obese FATZO mice treated with metformin (150 mg/kg/day) and an improvement in glucose tolerance with significant weight gain followed rosiglitazone (10 mg/kg/day) treatment. Administration of semaglutide (1-10 nmol/kg, SQ, q3d) elicited a loss of body weight, improvement in glucose tolerance and an acute reduction in feed intake.

EXAMPLE 1

This example shows that the FATZO mouse fed with the WDF diet would generate a model of significant liver disease which would meet the criteria for a more translational animal model of progressive NAFLD and NASH.

Methods

Animal Studies

Male FATZO mice (FATZO/Pco, n=88) were bred and maintained at the Crown Bioscience facility (Indianapolis, Ind.). Animals were housed individually and maintained on control diet of Purina 5008 chow (LabDiet, St. Louis, Mo.) and DI water ad libitum until study start. Mice at 8 weeks of age were randomized into 3 groups based on body weight. Additionally, to insure that all groups were matched according to insulin resistant state, fasting (6 hour) serum glucose and insulin levels prior to study start were used to calculate the additional randomization parameter (HOMA-IR). Randomized groups were assigned to 3 groups: 1. Control diet (CD) (n=32); 2. Western diet (D12709B, Research Diets, New Brunswick, N.J.) +5% fructose in the drinking water (WDF) for 5 months (n=32); 3. WDF with additional treatment of OCA (30 mg/kg, p.o., QD) from 2 months on diet for 15 weeks (n=8). Eight animals were terminated at the beginning prior to initiation of WDF to serve as a starting baseline for the experiment. Body weight and whole blood glucose (Stat Strip Express glucometer, Novo Biomedical; Waltham, Mass.) were recorded weekly. Whole body fat content (%) was assessed using qNMR (EchoMRI-500; Houston, Tex.). Eight animals from each group were sacrificed every month for the duration of the study. All animal experiments were approved by the Institutional Animal Care and Use Committee at Crown Bioscience—Indiana.

Biochemical Measurements

Mice were fasted (6 hours) prior to sacrifice and serum samples were obtained for clinical chemistry including glucose, insulin, cholesterol, triglycerides, AST and ALT (AU480 clinical analyzer, Beckman-Coulter; Brea, Calif.). Insulin content in plasma was determined from frozen sample using a mouse/rat insulin kit (Meso Scale Discovery K152BZC-3, Rockville, Md.). Liver triglyceride content was analyzed from samples snap frozen in liquid nitrogen by preparing 20% tissue homogenates in distilled water, placing them in Lysing Matrix D Tubes (MP Biomedicals, Santa Anna, Calif.) and spinning in a Fastprep-FP120 cell disrupter (Thermo Fisher Savant) for 30 seconds. Homogenates were kept cold and analyzed on a clinical analyzer (Beckman-Coulter AU480, Indianapolis, Ind.) within 30 minutes of preparation.

Histology

Tissue processing: The liver tissues were fixed in 10% neutral buffered formalin (NBF) at 4° C. for 24 hours followed by baths of standard concentrations of alcohol then xylene to prepare the tissues for paraffin embedding. After being embedded in paraffin and cooled, five-micron sections were cut and stained for routine H&E and Picric Sirius Red.

Whole slide digital imaging: The Aperio whole slide digital imaging system was used for imaging. The Aperio Scan Scope CS system was used (360 Park Center Drive, Vista, Calif.). The system imaged all slides at 20x. The scan time ranged from 1.5 minutes to a maximum time of 2.25 minutes. The whole images were housed and stored in their Spectrum software system and images were shot from the whole slides.

NASH scoring: The livers were evaluated using the NASH liver criteria for scoring. The recently published histological scoring scheme of the NASH Clinical Research Network (NASH CRN) is increasing in popularity by both clinical and research communities. In principle, this scoring system comprises of NAFLD Activity Score (NAS), fibrosis stage and identification of NASH by pattern recognition. The NAS can range from 0 to 8 and is calculated by the sum of scores of steatosis (0-3), lobular inflammation (0-3) and hepatocyte ballooning (0-2) from H&E stained sections. Fibrosis was scored (0-4) from picrosirius red stained slides. The NASH system is used for human liver 18 gauge biopsies. Steatosis, lobular inflammation, hepatocyte, balloon degeneration, fibrosis, NAS and the presence of NASH by pattern recognition were systematically assessed. In this study we evaluated one total cross section of liver per mouse in this study. This is about 15 times the size of an 18 gage human liver biopsy. The pathology score was determined as 0, +1, +2, or +3. The lesions were scored on location (periportal, centrilobular, and mid zonal) and fat accumulation (focal, periportal, and/or centrilobular). The other part of the score was distribution of the lesions: focal, multifocal and/or diffuse. Also, mild, moderate and severity of the lesions. These parameters made up the total NASH score.

Statistics

Treatment effects of WDF were compared to CD using One-Way or Repeat Measures ANOVA with multiple comparison t-test using Prism (GraphPad, version 7.01). Statistical differences were denoted as P<0.05. All values are reported at Mean±SEM. HOMA-IR was calculated using the following equation: fasted insulin (µIU/ml)×fasted glucose (mg/dL)/22.5. All assigned animals completed the study.

Results

Figure 1B:
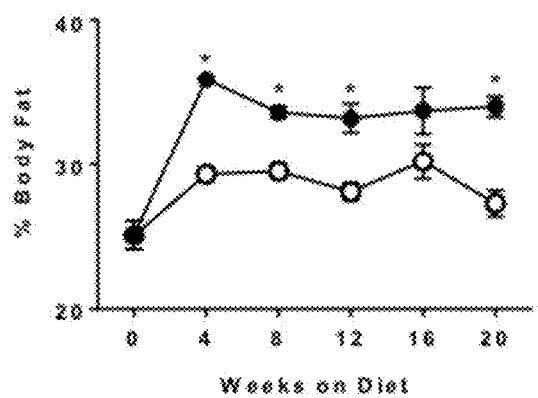
Figure 1C:
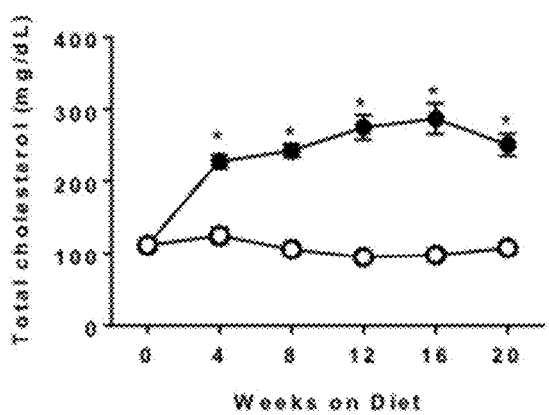
Figure 1D:
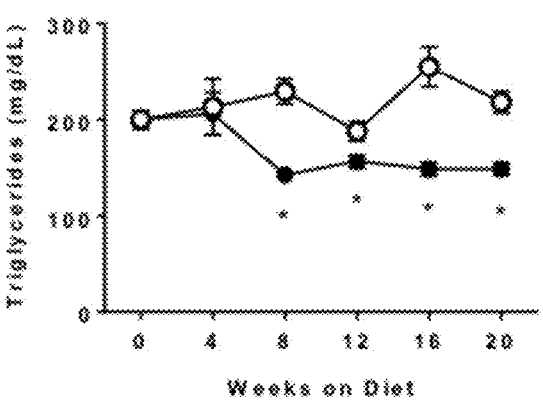

WDF Exacerbated Metabolic Disorders, Impaired Liver Function and Histological Changes Assembling to NAFLD/NASH in FATZO Mice The FATZO mice fed WDF showed a significantly greater increase in body weight (FIG. 1A), associated with a significant increase in body fat compared to the age-matched CD fed mice (FIG. 1B). Blood cholesterol levels were almost 2.5 times higher in WDF group than CD controls after 4 weeks on diet and the levels were consistently higher in WDF group throughout the diet induction period (FIG. 1C), though triglyceride levels were slightly lower (FIG. 1D) in the WDF group.

Figure 1E:
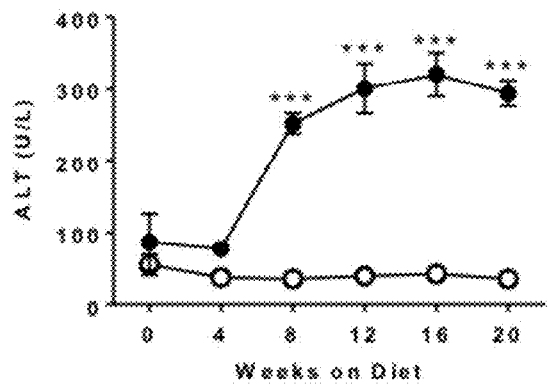
Figure 1F:
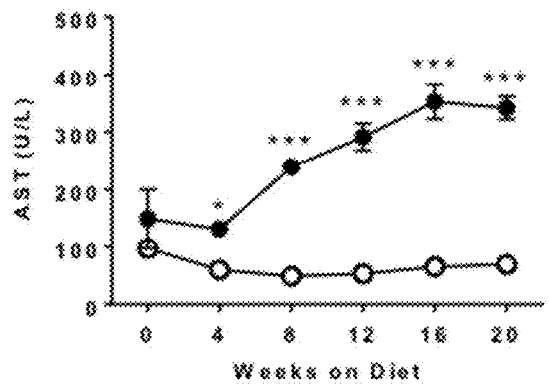
Figure 1G:
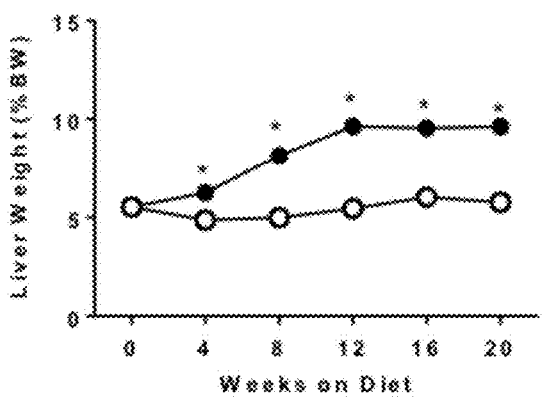
Figure 1H:
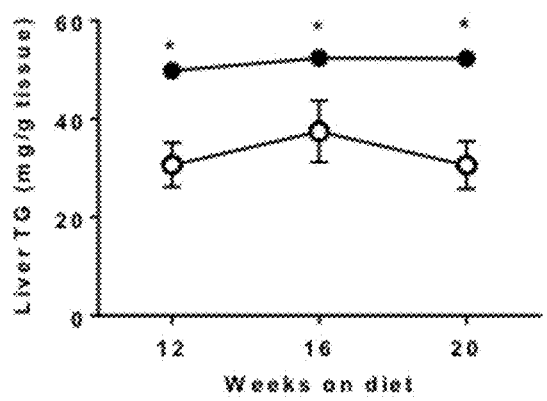

Metabolic stress on the livers of mice fed WDF caused significant elevation in the liver enzymes, with evidence of almost 6 and 4-fold higher in alanine aminotransferase (ALT) (FIG. 1E) and aspartate transaminase (AST) (FIG. 1F) levels respectively over the 20 weeks of diet exposure compared to that in control diet (CD) fed mice. Liver weight increased over time in both groups, which, however, was significantly higher in the western diet with fructose (WDF) than CD group (FIG. 1G). Liver TG contents measured at weeks 12-20 from mice fed WDF showed 2 folder differences with significantly higher levels compared to that in the mice fed CD (FIG. 1H).

FATZO mice fed WDF developed fatty liver characterized by progressive steatosis, hepatocellular ballooning, lobular inflammation and early stages of fibrosis.

Figure 2:
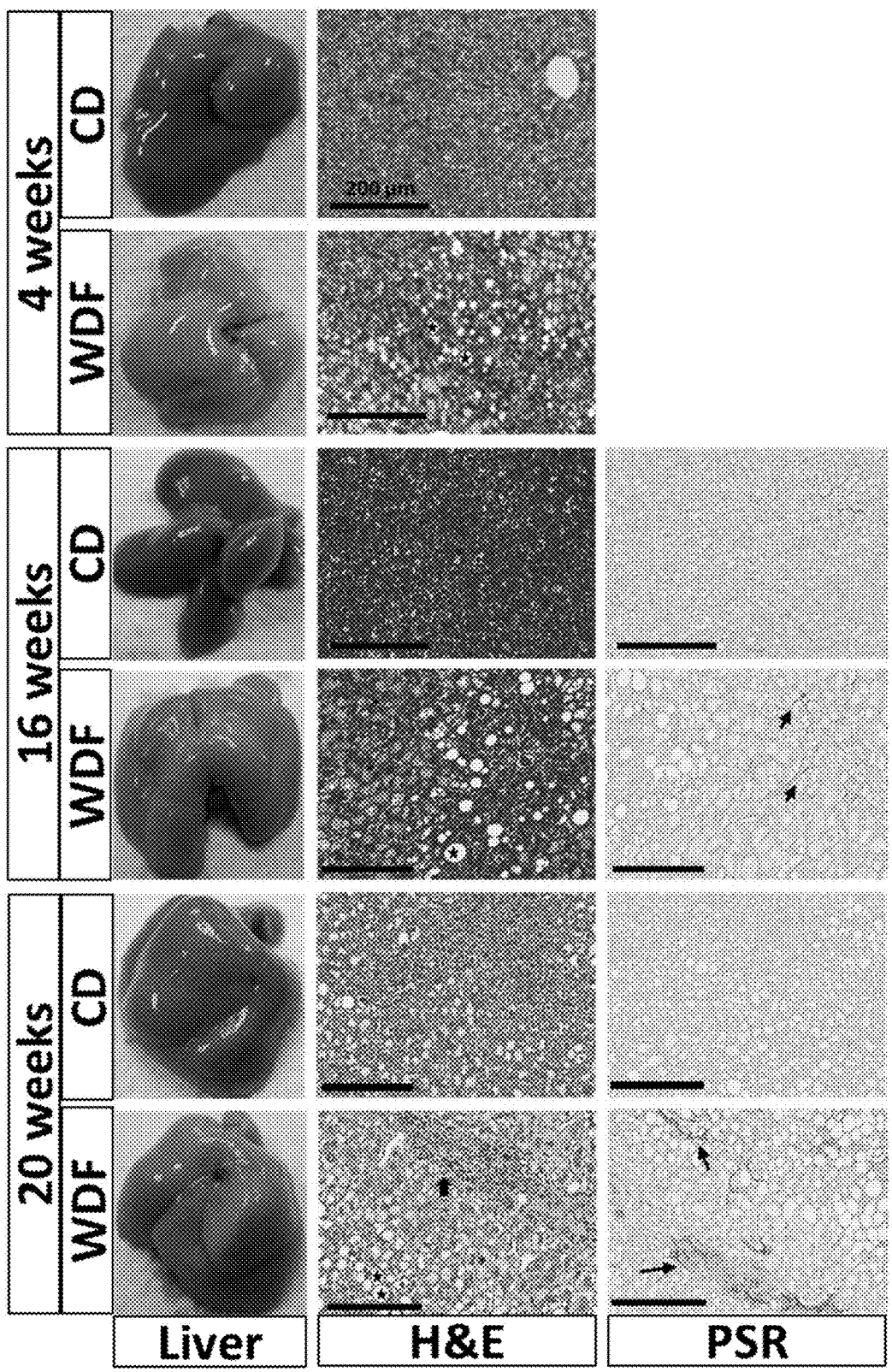
FIG. 2 shows histological characteristics of NAFLD/NASH in the FATZO mouse fed WDF. Representative images of the H&E and Picro Sirius Red (PSR) staining of livers removed from FATZO mice fed WDF or CD for 4, 16 and 20 weeks. ★Denotes steatosis, ✱ denotes ballooning, ✝ denotes lobular inflammation and ↑ denotes fibrosis.

During the early progression of NAFLD, the livers from FATZO mice fed WDF were very pale in color upon necropsy compared to that of CD fed mice (FIG. 2). H&E staining demonstrated fully involved steatosis with ballooning as early as 4 weeks on WDF diet compared to CD. Over the time, FATZO mice exhibited a progressive worsening of NAFLD. At each time point, the livers of mice fed WDF were paler in color than the corresponding FATZO mice fed CD. Significant histological changes indicative of NAFLD (steatosis, hepatocellular ballooning, lobular inflammation) including mild fibrosis were seen in the liver sections from the group after 16 weeks on WDF diet compared to the corresponding CD fed group (FIG. 2).

Figure 3A:
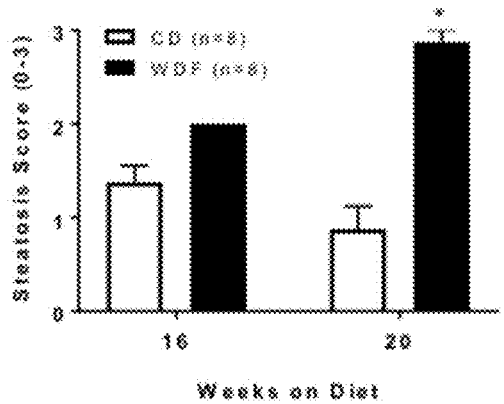
FIGS. 3A-3E show the NASH scoring of the liver from WDF or CD fed FATZO mice for 16 and 20 weeks.
Figure 3B:
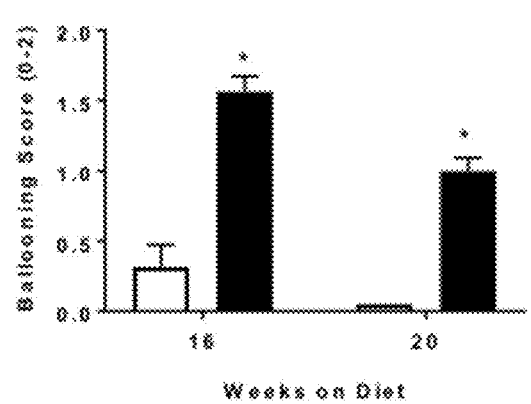
Figure 3C:
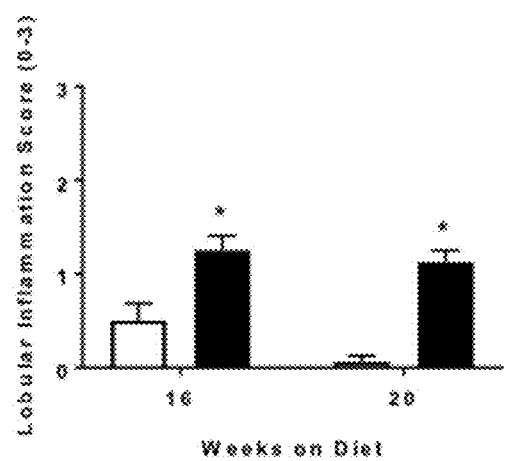
Figure 3D:
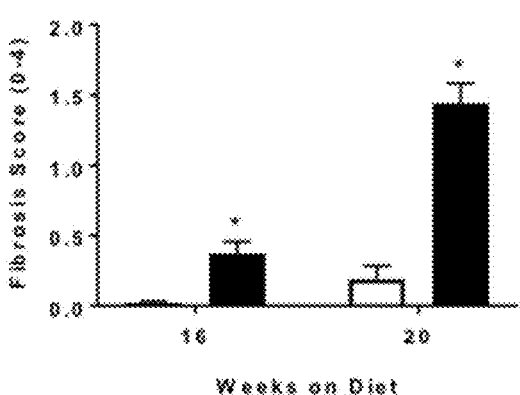
Figure 3E:
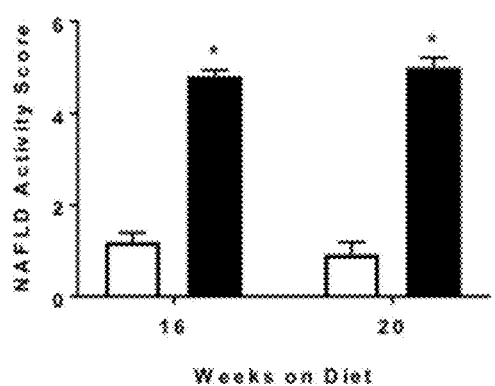

When sections were assessed for NASH activity scores, the livers from WDF fed mice exhibited significantly higher scores for steatosis (FIG. 3A), hepatocellular ballooning (FIG. 3B), lobular inflammation (FIG. 3C) and fibrosis (FIG. 3D) comparing to the corresponding livers from the CD fed mice. In looking at a composite NAFLD activity score (NAS), the livers from WDF fed mice demonstrated significantly more pathological findings when compared to the livers from CD fed mice (FIG. 3E).

OCA Improved Liver Function and Hepatic Ballooning in FATZO Mice Fed WDF

Figure 4G:
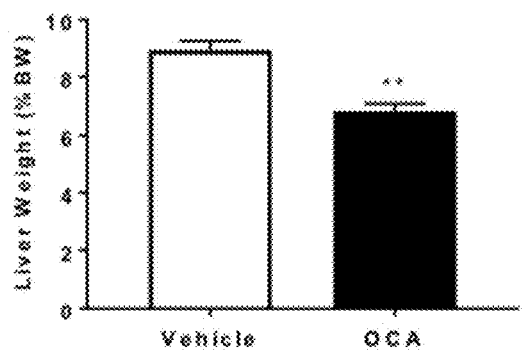
Figure 4H:
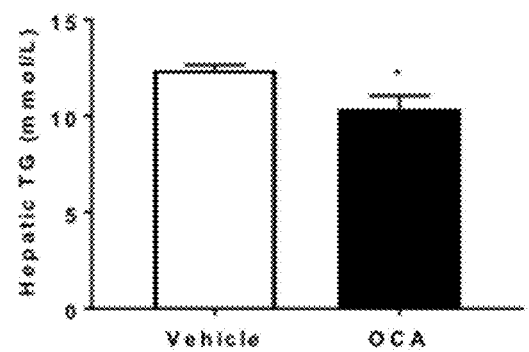

Treatment of OCA (30 mg/kg, QD) in FATZO mice on WDF from 8 weeks on diet for 15 weeks had no impact on body weight (FIG. 4A) or blood TG levels (FIG. 4B). By contrast, OCA treatment alleviated the elevation of blood total cholesterol (FIG. 4C) and LDL (FIG. 4D), resulting in significantly lower levels compared to vehicle controls. In addition, improvement in liver function could be seen as early as 4 weeks after OCA treatment, as blood ALT (FIG. 4E) and AST (FIG. 4F) levels in OCA treatment group were dramatically lower than its own pretreatment baseline as well as the CD fed mice. After treatment of OCA for 15 weeks, relative liver weight (FIG. 4G) and hepatic TG levels decreased significantly compared to vehicle controls (FIG. 4H).

Figure 6A:
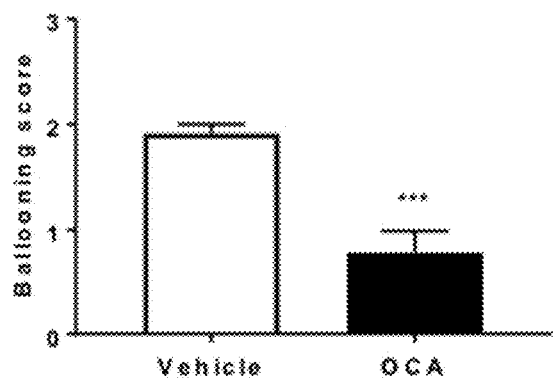
FIGS. 6A-6E show the histological improvement of WDF fed FATZO mice treated with OCA.
Figure 6B:
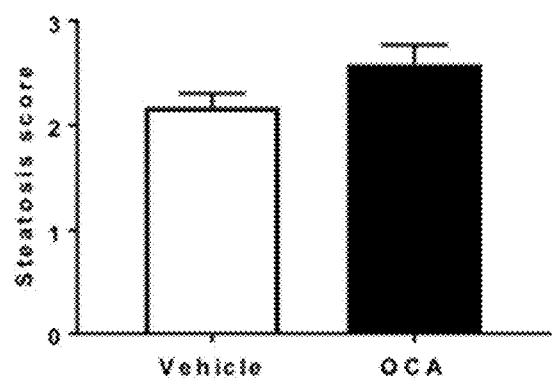
Figure 6C:
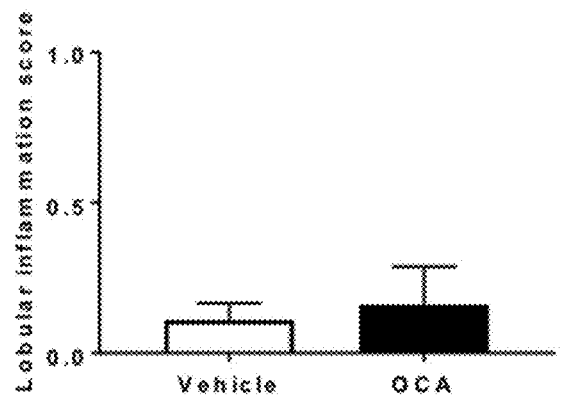
Figure 6D:
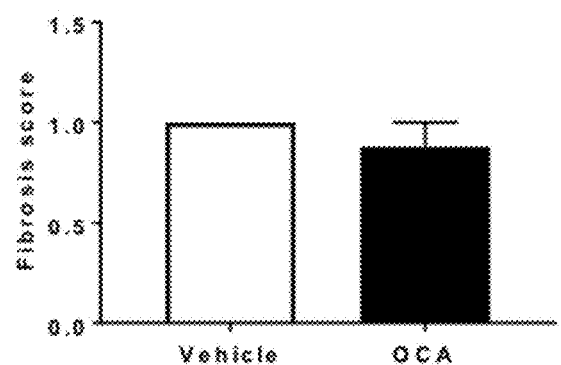
Figure 6E:
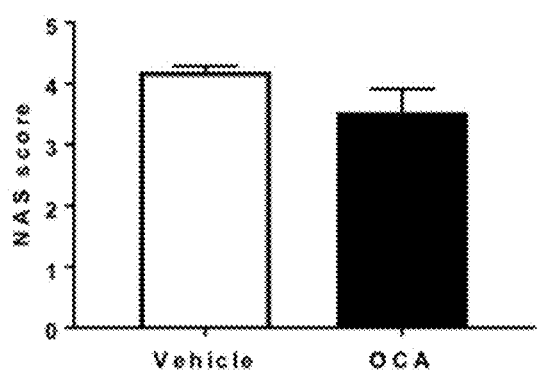

When liver histology was evaluated (FIG. 5), OCA treatment tended to improve NAS score (FIG. 6E) with significant alleviation in numbers of foci showing hepatic ballooning (FIG. 6B). The changes in other components of NAS score, such as steatosis (FIG. 6A), lobular inflammation (FIG. 6C), and fibrosis (FIG. 6D) were not obvious.

In conclusion, the polygenic FATZO mouse model when fed a WDF diet developed progressive NAFLD and NASH similar to humans. The FATZO WDF model of NAFLD and NASH represents another scientific tool for the advancement of research in this area that is potentially more translatable to human disease than current models.

EXAMPLE 2

This example illustrates the correlation of disease severity with body weight and high fat diet in the FAZTO mouse.

Materials and Methods

FATZO Production

FATZO mice in the breeding colony were maintained on Purina 5008 rodent diet and reverse osmosis water. Mice were bred between 6 and 10 weeks of age (optimally 7-8 weeks old). Animals were housed in a light (12 hr light/12 hr dark) and temperature (25° C.) controlled environment.

The Effect of High Fat Diet

Male FATZO/Pco mice (n=48) were weighed (24-43 g) at 6 weeks of age and transferred from the CBIN colony (Crown Bioscience—Indiana, Indianapolis, Ind., USA) to Lilly Research Laboratories (Indianapolis, IN, USA) at 6-8 weeks of age. After acclimation, FATZO mice averaging 10 weeks of age were assigned to groups based on their 6-week weights as follows: Low BW (low weight, 23-26.9 g), Mid BW (mid weight, 27-29.9 g) and High BW (high weight, >30 g). At the initiation of the study, the average weights of the groups of 10-week old mice were: Low BW (29.4±0.7 g), Mid BW (35.7±0.7 g) and High BW (38.9±0.7 g). Mice in each weight group were randomized into 2 subgroups (n=8/subgroup) that were fed either Purina 5008, 16% fat chow (Chow) or D12492, 60% fat diet from Research Diets (HFD, New Brunswick, N.J., USA). Body weight was recorded weekly; whole blood glucose (AccuChek Aviva meters) levels were recorded weekly from 10 to 18 weeks of age and again at 21 weeks of age. Blood was collected from mice at 10, 12, 14, 18 and 21 weeks of age and plasma was prepared for insulin analysis. Blood samples for glucose and insulin were obtained by tail snip in the fed state. An oral glucose tolerance test (OGTT) was performed following a 17 hour fast in 18-week old mice to assess glucose disposal; glucose and insulin levels were assayed from samples taken at 0, 15, 30, 60 and 120 min post-glucose load (3 g/kg, PO). Plasma from blood samples collected throughout the study and during the OGTTs was analyzed for insulin using the mouse/rat insulin assay kit (K152BZC, Meso Scale Discovery, Rockville, Md., USA).

Animals were euthanized with $CO_2$ at 21 weeks of age. Each pancreas was dissected, weighed, snap frozen in liquid $N_2$ and placed in EtOH-HCl (5 ml) extraction buffer (23.5 parts water, 75 parts ethanol, 1.5 parts concentrated HCl) and kept at 4° C. After thorough mincing with a polytron homogenizer, the pancreas was extracted in the buffer by overnight shaking at 4° C. The tissue was separated from the extract by centrifugation and diluted for insulin analysis with Earle's Balanced Salt Solution (EBSS) with 0.1% BSA. These extracts were also analyzed using the mouse/rat insulin assay kit (K152BZC, Meso Scale Discovery, Rockville, Md., USA).

Leptin Levels and the Effect of Leptin on Food Intake

Two age groups of male FATZO mice were selected for leptin levels and the effect of leptin on food intake. Additional age matched groups of C57BL/6 were bled for leptin levels. Animals were acclimated to reverse light cycle for 7 days before being put on protocol. Thirty to sixty minutes before lights were turned out, blood was collected for leptin levels from 5 (N=7) and 11 (N=8) week old male FATZO mice and from male C57BL/6 at approximately the same ages (N=6). Serum was prepared from tail blood and leptin levels were analyzed (Meso Scale Discovery, K152BYC, Rockville, Md., USA). After blood collection, animals were given saline or leptin injections (10 mg/kg) and food intake data was recorded for the first 4 hours of darkness.

Statistics

Except where mentioned, all data are presented as Mean±SEM. Statistical analysis was done using Prism for Windows (version 6.07 GraphPad, San Diego, Calif., USA). When comparing groups, one-way ANOVA followed by Sidak's multiple comparisons test were done; two-way ANOVA followed by Sidak's multiple comparison tests were performed when groups were compared over time. Linear regression was performed on paired (6-week body weight versus 14-week glucose and insulin) followed by a correlation analysis.

Results

FATZO Production

Development and breeding of the FATZO mouse model required some special conditions. Based on the rapid weight gain of these animals, the breeding ages are more limited than with usual mouse colonies. Breeding was most successful when done between 7-8 weeks of age. Successful litters from lower body weight animals could be produced over a longer period of time; however, this practice resulted in lower body weight offspring and increased the potential for drift towards a less obese model. Older, heavier animals could be bred, but this resulted in fewer pregnancies and lower production. The breeding and housing at higher temperatures was also an important consideration since higher temperatures, closer to thermo-neutral, enhanced weight gain and disease expression. An analysis of 53 litters of FATZO mice indicated a negative correlation of litter size with male pup body weights (r=−0.6986, p<0.0001). Since larger litters contained lower body weight animals, restricting litter size resulted in heavier offspring. Despite normalization of litter size, variation in animal weights was still observed.

Animal Weights

Figure 7A:
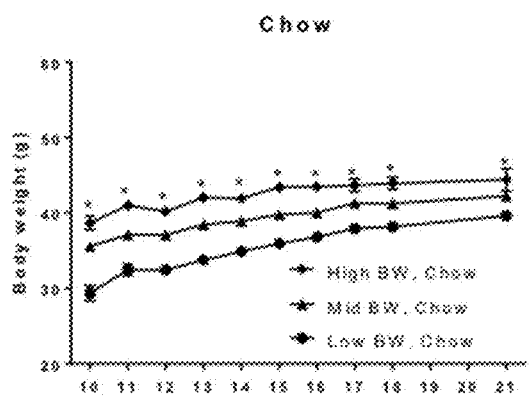
FIGS. 7A-7F show the effects of initial weight and diet on body weight, glucose and insulin levels. The top figures illustrate Body weight gains of animals on the Chow diet (FIG. 7A) and HFD (FIG. 7B). The middle panels (FIGS. 7C, 7D) demonstrate the effects of the two diets on glucose levels. Insulin levels in Chow (FIG. 7E) and HFD (FIG. 7F) groups are illustrated in bottom panels. The * in FIGS. 1A and 1B indicates that all weight groups are statistically different from each other at all of the time-points with each diet. Statistical differences from the other groups (FIGS. 1C-1F) are identified by * while the + sign identifies differences between the highest and lowest values (two-way ANOVA followed by Sidak's multiple comparison test, * or ⁺p<.05). Additional differences between diets in each weight category are summarized in the text.
Figure 7B:
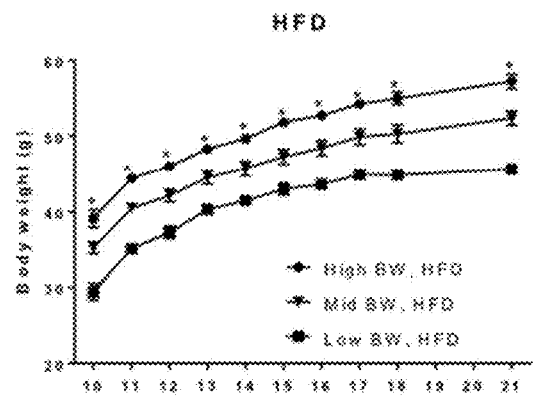

Animals were grouped based on their 6-week (initial) weights to determine the influence of early weight on subsequent weight gain, insulin levels, glucose tolerance and hyperglycemia. The averages of the weight groups within each diet remained significantly different from each other at all time-points with both Chow and HFD diets (FIGS. 6A and 6B). The mice fed the HFD (FIG. 7B) all gained weight more rapidly than the weight-matched, Chow-fed animals (FIG. 7A). Two-way RM ANOVA demonstrated significant differences in weight between the Chow and HFD with each weight category at every time point after diet initiation (p<.0005). Table 2 demonstrates that all weight groups of mice on HFD ate less mass of the diet than the animals on Chow. However, the High BW, HFD group had higher caloric intake compared to the High BW Chow fed group.

TABLE 2

Food consumption

| | Cumulative Food Consumption (g) | Cumulative Caloric Intake (kcal) |
|---|---|---|
| Low BW, Chow | 230.6 ± 4.2, n = 8 | 807.1 ± 14.8, n = 8 |
| Low BW, HFD | 159.4 ± 3.3, n = 8* | 835.2 ± 17.5, n = 8 |
| Mid BW, Chow | 241.9 ± 4.8, n = 8 | 846.5 ± 16.7, n = 8 |
| Mid BW, HFD | 172.4 ± 5.9, n = 8* | 903.4 ± 30.8, n = 8 |
| High BW, Chow | 268.6 ± 8.1, n = 7 | 940.0 ± 28.3, n = 7 |
| High BW, HFD | 204.8 ± 3.2, n = 8* | 1073.3 ± 16.9, n = 8* |

*indicates statistical differences between Chow and HFD in the weight group.

Glucose Levels

Figure 7C:
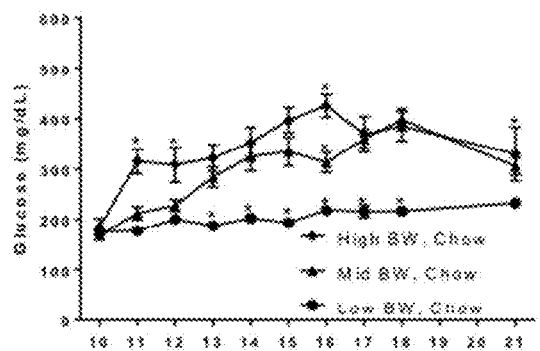
Figure 7D:
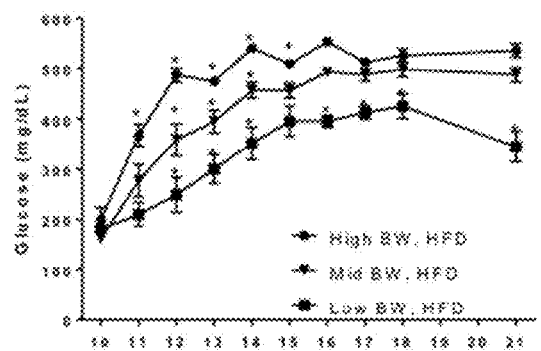

Despite similar glucose levels between the weight groups at 10 weeks of age (FIGS. 7C and 7D), glucose differences became evident over time in both the Chow and HFD groups. The initial rise in glucose levels for both the Chow (FIG. 7C) and HFD (FIG. 7D) groups correlated with initial body weight. The Chow fed, High BW and Mid BW groups had comparable increased glucose levels from 13 to 21 weeks of age while Low BW Chow group remained at close to baseline levels for the duration of the experiment (FIG. 7C). Similarly, the 2 heaviest groups of HFD animals attained the highest glucose levels over time, while the low BW group had significantly lower glucose levels over the course of the experiment (FIG. 7D). As with weight, two-way RM ANOVA identified significant differences in glucose curves between the Chow and HFD with each weight category (p<.005). Sidak's multiple comparisons test also demonstrated significant differences between the diets at all ages (p<.01) except at 10-12 weeks of age in the Low BW groups and at 10, 11, 15 and 18 weeks in the Mid BW and 10 and 11 weeks in the High BW Groups.

Insulin Levels

Figure 7E:
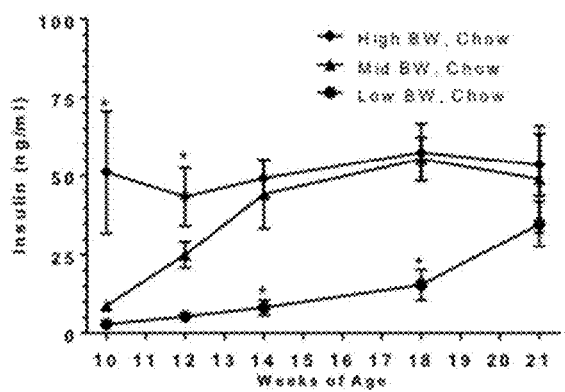
Figure 7F:
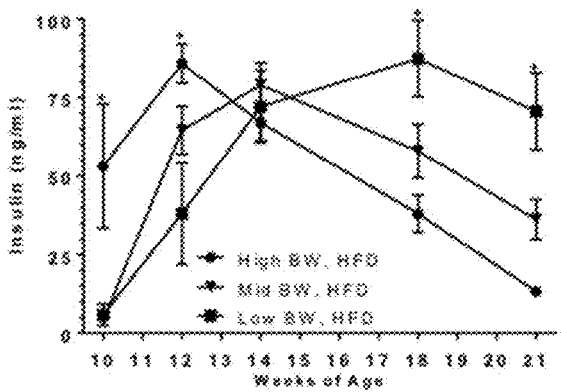

The results demonstrate a positive relationship between body weight and plasma insulin levels in the 10-12 week data. Initial 10-week insulin levels of the High BW groups were significantly higher than the two lower body weight groups (FIGS. 7E and 7F). In the Chow fed/High BW group, the average insulin levels did not change over time (FIG. 7E). However, in both the Mid BW and Low BW groups, insulin levels increased over time with the Mid BW group becoming similar to the High BW group at 14 weeks of age and the Low BW group at 21 weeks (FIG. 7E). In contrast, the insulin levels in the HFD groups increased dramatically over the first 4 weeks of HDF with the average insulin levels becoming similar at 14 weeks of age. Subsequently, the insulin levels decreased in the two higher weight groups (FIG. 7F).

Glucose Tolerance

Figure 8A:
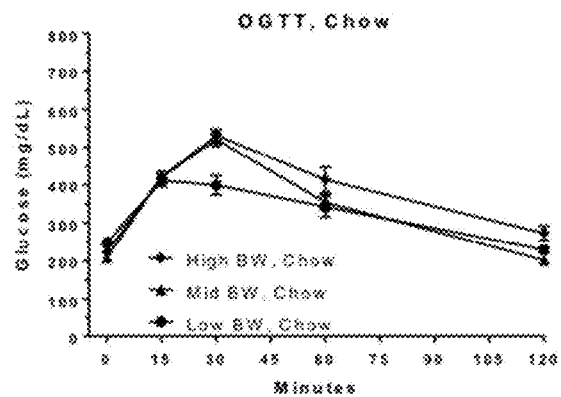
FIGS. 8A-8F show the effects of initial weight and diet on fasting glucose and glucose disposal in an OGTT. The top figures show glucose responses in the OGTT for mice fed the Chow diet (FIG. 8A) and the HFD (FIG. 8B). Baseline glucose levels, after a 17 hour fast in the Low, Mid and High BW groups of mice fed the Chow diet (FIG. 8C) while glucose levels are significantly higher in the Mid BW and High BW animals on the HFD (FIG. 8D). The figures in the two lower panels illustrate the glucose AUC from the OGTT for animals in each of the body weight groups when fed Chow diet (FIG. 8E) and HFD (FIG. 8F). (one-way ANOVA followed by Sidak's multiple comparison tests. + denotes a statistical difference compared to the Low BW and * denotes statistical from all other group, p<.05).
Figure 8B:
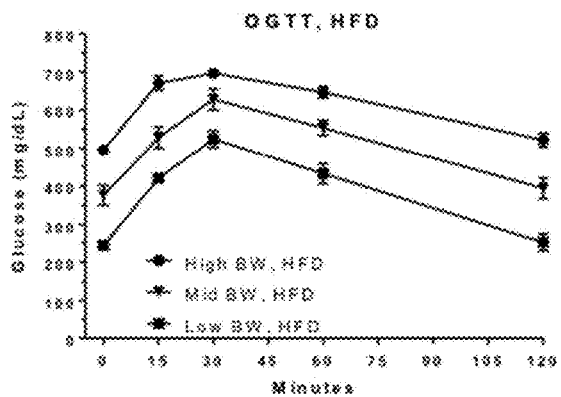
Figure 8C:
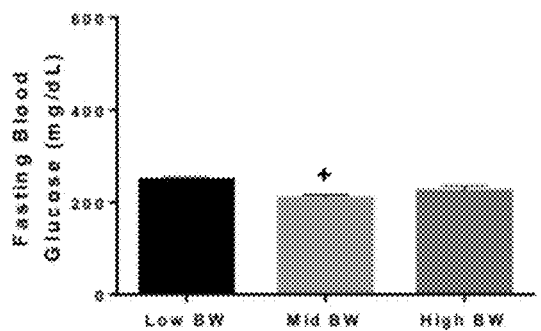
Figure 8D:
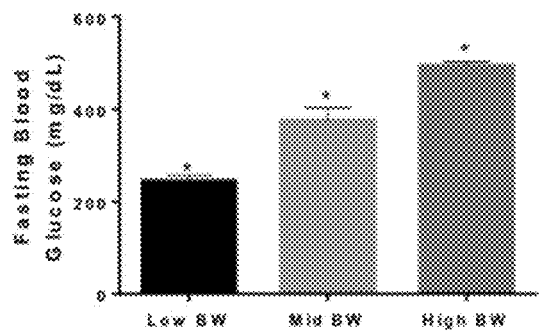
Figure 8E:
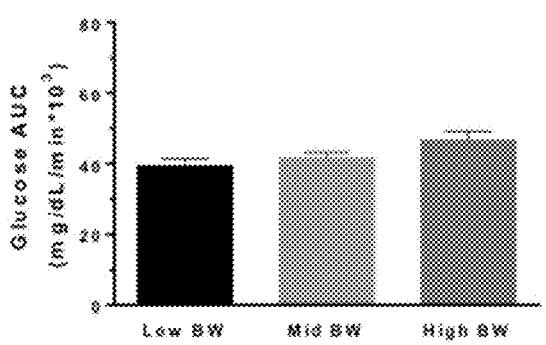
Figure 8F:
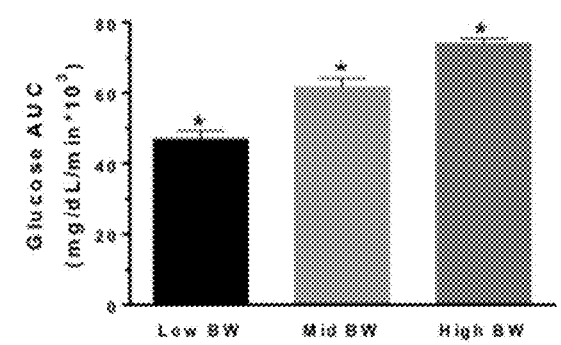
Figure 9A:
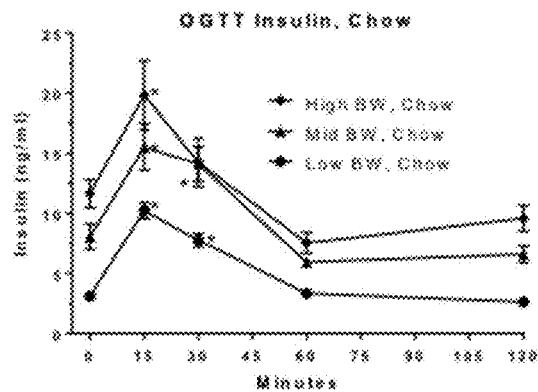
FIGS. 9A-9E show the effects of initial weight and diet on insulin levels during the OGTT. This graph illustrates the insulin response to a glucose load at 18 weeks in the Low BW, Mid BW and High BW groups when fed the Chow diet (FIG. 9A) or the HFD (FIG. 9B). The * in FIGS. 9A and 9B indicates significant increases from baseline for that group (two-way ANOVA followed by Sidak's multiple comparison tests). The insulin AUCs (FIGS. 9C, 9D) for the above OGTTs (FIGS. 9A, 9B) are also illustrated; the ** indicates a significant difference between the Low BW group and the other two groups (one-way ANOVA followed by Sidak's multiple comparison tests). The lowest panel (FIG. 9E) illustrates the insulin content of the pancreas from the different weight groups on the two diets at 21 weeks. The effect of diets was tested in respective weight pairs (High BW, Mid BW and High BW); † denotes there was a statistically significance difference between the two diets in the High BW groups (one-way ANOVA followed by Sidak's multiple comparison tests). *, **, † denotes statistical significance at the level p<.05).
Figure 9B:
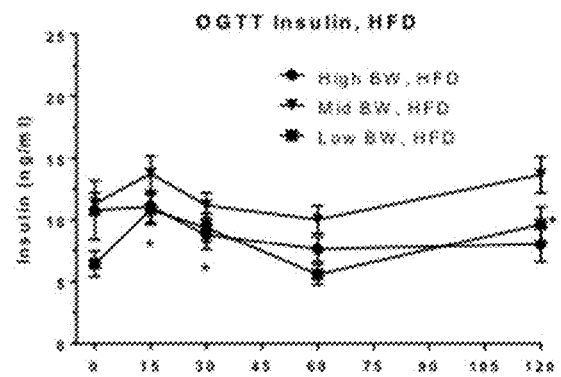
Figure 9C:
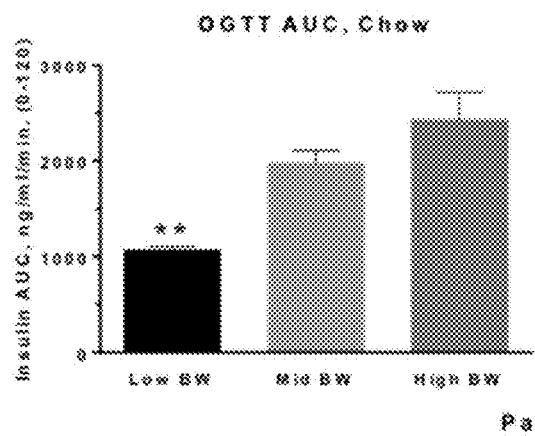
Figure 9D:
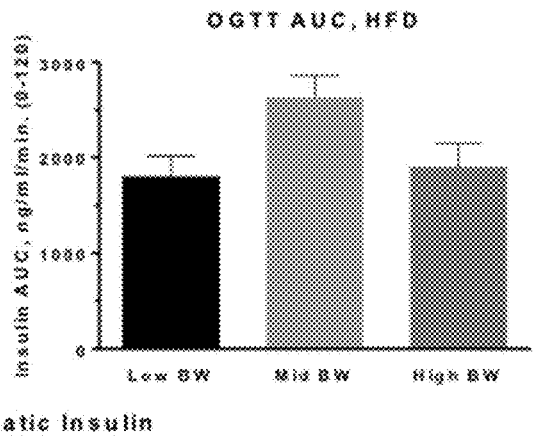

An OGTT was performed when the animals were about 18 weeks of age (FIGS. 8A and 8B). FIGS. 8C and 8D show the fasted glucose levels after an overnight fast. These figures illustrate that fasted glucose levels in the Chow-fed groups are quite similar at baseline (FIG. 8C), while they remain significantly elevated in the two heavier HFD groups (FIG. 8D). The Chow fed glucose levels in the OGTT showed a significant excursion that was greater than what one would typically see in a control mouse (~30*10$^3$ in comparable studies, PCO unpublished) but with the overnight fast, the glucose levels fall close to fasting levels in 120 minutes; the AUC data demonstrated similar values for the three groups (FIG. 8E). The Mid and High BW, HFD groups demonstrate elevated fasting glucose levels (FIG. 8D) and delayed glucose disposal (FIGS. 8B and 8F). Serum insulin levels were determined for the time-points in the OGTT. The insulin response in the Chow-fed groups showed a transient increase after the glucose load (FIG. 8A) while the animals fed the HFD had a blunted response (FIG. 8B). The fasting insulin levels in the Chow-fed groups were increased relative to body weight. The insulin levels in response to the glucose load were significantly increased from baseline at 30 and 60 minutes (FIG. 9A). The AUC for insulin during the OGTT in the Chow fed groups (FIG. 9C) also demonstrated that there was a relationship between weight and the AUC with the lightest groups having a significantly lower insulin AUC. In the HFD groups, there was no increase from baseline insulin levels in the High and Mid BW groups, but there were significant increases from baseline in the Low BW group (FIG. 9B).

Pancreatic Insulin

Figure 9E:
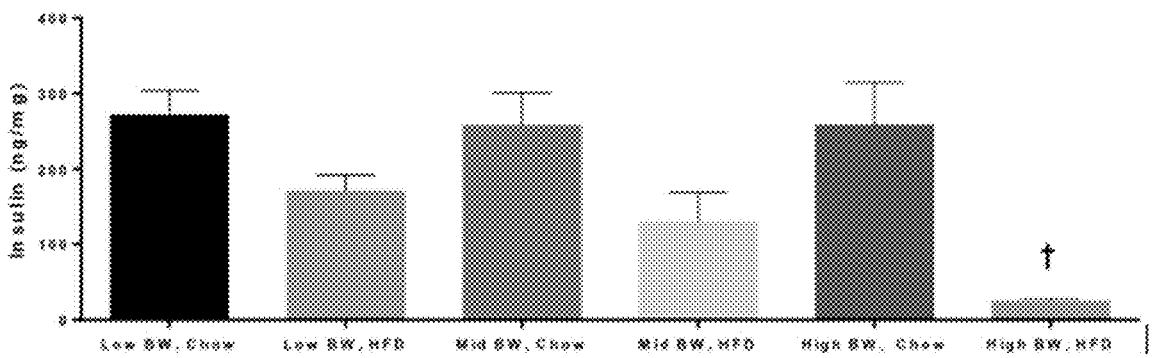

At the end of the experiment pancreases were removed and insulin content was determined. In accordance with plasma insulin data, pancreatic insulin was also significantly reduced in the HFD, High BW group when compared to the Chow, High BW group (FIG. 9E).

Body Weight, Glucose and Insulin Correlation

Figure 10A:
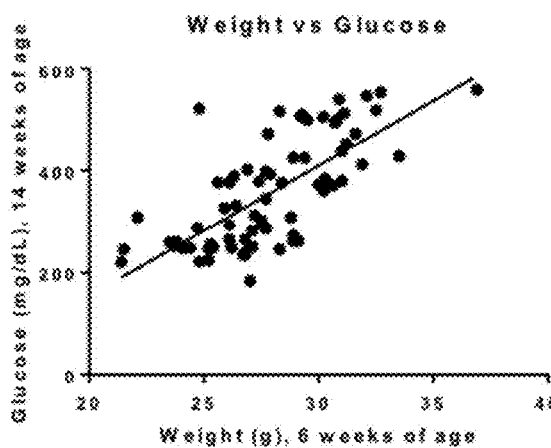
FIGS. 10A and 10B show that weight correlated with glucose and insulin, Glucose (FIG. 10A) and insulin (FIG. 10B) levels at 14 weeks were plotted and analyzed according to the animal weights at 6 weeks of age (weight vs glucose, r=0.7033, p<.0001; weight vs insulin, r=0.5317, p<.0001).
Figure 10B:
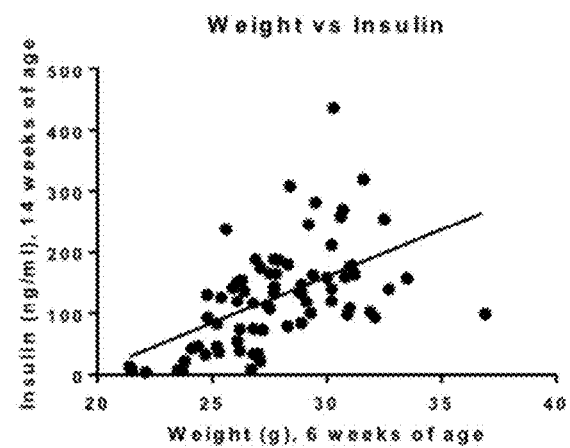

Retrospective analysis of a cohort of 73 FATZO male mice demonstrated that glucose and insulin in 14-week old mice were positively correlated with body weights of 6-week old mice (FIG. 10).

Leptin Levels and the Effect of Leptin on Food Intake

Figure 11A:
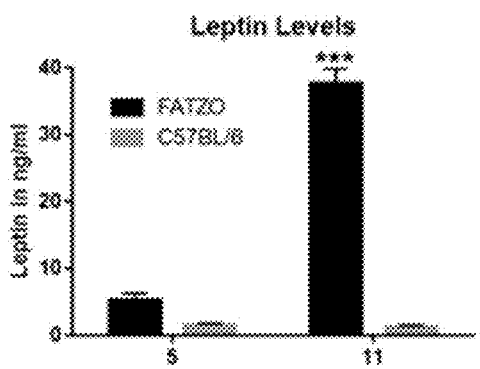
FIGS. 11A and 11B show that leptin levels and the effect of leptin on food intake, Leptin levels (FIG. 11A) and the effect of leptin on food intake (FIG. 11B) at two ages are illustrated in this figure (one-way ANOVA followed by Sidak's multiple comparison tests). Statistical differences from the other groups are denoted at p<.001() and p<.0001(*).
Figure 11B:
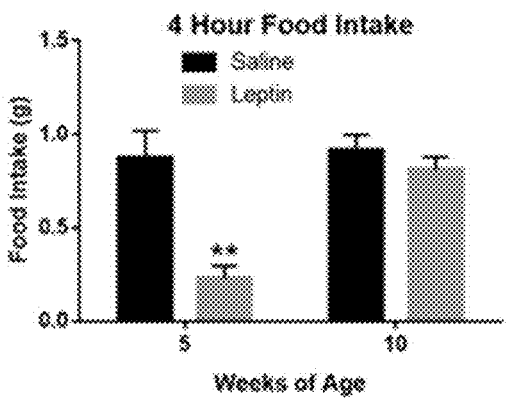

At 5 weeks of age leptin levels are not significantly different between FATZO and C57BL/6 mice but as the FATZO mice become more obese their leptin levels increase rapidly while the C57BL/6 mice remain low and are not significantly different from 5 week-old animals (FIG. 11A). Food consumption is significantly reduced with leptin injections in young FATZO animals but as the endogenous leptin levels increase at 10 weeks of age there is no significant reduction in food intake (FIG. 11B).

In conclusion, the FATZO mouse exhibited dysfunctional glucose homeostasis in a wide range of severities based on body weight. Within an age group, leaner animals exhibited impaired glucose handling while heavier animals generally displayed more severe glucose intolerance. This phenotypic variability enables the selection of animals in the desired stage of metabolic syndrome/type 2 diabetes. Body weight inclusion criteria can be used to design studies directed at slowing progression (Mid BW) or treatment of (High BW) diabetes. The FATZO mouse is proposed as a novel animal model for the study of obesity/metabolic syndrome and its progression. The glucose stimulated insulin release was blunted in all weight groups fed HFD. This lack of response after a glucose load suggests that the pancreatic beta cells have lost their ability to respond effectively to elevated glucose. Introduction of a high fat diet promotes the development of more severe diabetes characterized by hyperglycemia, decreased insulin release and sensitivity which could ultimately lead to beta cell failure.

EXAMPLE 3

This example illustrates the glucose dysregulation and response to common anti-diabetic agents in the FATZO mouse Methods Age Related Changes in Glucose Homeostasis FATZO/Pco mice were bred and maintained at PreClinOmics (now Crown Bioscience—Indiana). Male mice (n=72) were housed 2 per cage. Room temperature was monitored and maintained at 72-77° F. with the light cycle set at 12 hours (0600-1800 hr). Purina 5008 standard rodent chow and house water were provided ad libitum. Body weight, fed blood glucose and insulin were recorded at 2-week intervals from 6-22 weeks of age within two hours of the room lights coming on. Serum glucose was analyzed in fresh plasma using AU480 clinical analyzer (Beckman-Coulter, Brea, Calif., USA). Insulin content in plasma was determined from frozen sample using a mouse/rat insulin kit (Meso Scale Discovery K152BZC-3, Rockville, Md., USA).

Comparison to Age Matched Controls

In a parallel study, body composition and glucose disposal in male FATZO mice (n=6) were evaluated and compared to age matched control C57BL/6J mice (n=6); Purina 5008 was the diet for both groups. Oral glucose tolerance tests (OGTT) were performed every 4 weeks from 6-18 weeks of age. Following a 12 hour fast, glucose (2 g/kg) was administered orally by gavage. Blood samples were taken via tail clip and glucose analyzed by StatStrip (Xpress, Data Science International, MN, USA) at 0, 30, 60, 90 and 120 minutes post-glucose load. The area of the blood glucose response curve corresponding to each animal was calculated by the trapezoid method [37], using each individual baseline blood glucose measurement prior to glucose administration as reference (t=0). The sum of the trapezoidal areas between the 0, 30, 60, 90 and 120-minute time points corresponding to each animal was calculated to obtain the area under the curve (AUC). Serum triglycerides were assayed in the fed state in 6, 10 and 14 week old animals.

Body composition was assessed in conscious mice every 4 weeks from 6-18 weeks of age using qNMR (EchoMRI-700, Houston, Tex., USA). Whole body qNMR was performed just prior to initiation of fasting for OGTT. All data are presented as Mean±SEM (n=6/group).

Response to Metformin and Resiglitazone

Male FATZO mice (9 weeks of age, n=40) were maintained on Purina 5008 regular rodent chow and reverse osmosis water ad libitum. Mice were housed 3 per cage and acclimated to study environment for 7 days prior to study. At 10 weeks of age, mice were fasted for 6 hours, body weight was recorded and an OGTT performed. Glucose and insulin were assayed at 0, 30, 60, 90, 120 and 180 minutes following a 2 g/kg glucose load. Glucose concentrations were obtained from StatStrip glucometer and insulin was assayed at each time-point using the insulin kit mentioned above. Insulin sensitivity index (ISI) was calculated using a formula modified from Matsuda and DeFronzo [39] by changing the numerator to 10,000 and using glucose and insulin AUCs instead of average glucose and insulin levels (100,000/square root of [fasting glucose x fasting insulin]×[glucose AUC×insulin AUC during OGTT]).

Animals were randomized into 3 groups of 10 based on baseline ISI and body weight. Groups were assigned to receive either vehicle (0.5% CMC, 0.1% Tween 80), rosiglitazone (KEMPROTEC Limited, U.K.) (10 mg/kg/day) or metformin (Toronto Research Chemicals, North York, Ontario, Canada) (150 mg/kg/day). Compounds were administered orally once daily by gavage for 8 weeks. Body weight was recorded weekly.

Following 8 weeks of treatment, OGTT was repeated one hour after compound administration. Whole blood was taken from tail clip and processed to serum. Treatment effects on glucose disposal, fed serum glucose, HbA1c, and ISI were compared to vehicle.

Response to GLP-1 Agonist Semaglutide

Male FATZO mice (n=32) were housed one per cage and maintained at constant room temperature (77-78° F.) and fed Purina 5008 regular rodent chow from weaning until 12 weeks of age. At this time, a reversed 12-hour light cycle (to accommodate for glucose and OGTT activities) was initiated (dark cycle 0700-1900 hr) and the diet was changed to Purina 5015 for the remainder of the study. Animals were acclimated to this environment for 2-3 weeks. During the last 5 days of acclimation, animals were acclimated to handling by daily SQ administration of phosphate buffered saline (PBS). Twenty-four hours prior to study start, baseline values (whole blood glucose and body weight) were obtained 2-3 hours into the dark cycle. Blood sample was obtained in the fed state by tail clip for whole blood glucose level (StatStrip). Animals with body weight≥40.0 g and fed glucose level of ≥250 mg/dL were accepted for study, randomized to 4 groups of 8 based on body weight and fed glucose and assigned to receive either vehicle (20 mM citrate buffer, pH 7), or semaglutide 1.0, 3.0 or 10.0 nmol/kg, SQ, q3d (one dose every three days). Semaglutide was synthesized by Eli Lilly and Company, Indianapolis, Ind. using protocols similar to published. Compound was delivered just prior to dark cycle (0600-0700 hr) and continued for six doses. Dose volume was adjusted daily to maintain 10 ml/kg. Twenty-four hours following the last dose, animals were subjected to a 6 hour fast (0800-1400 hr) for performance of an oral glucose tolerance test (OGTT). Blood samples were obtained via tail clip at 0, 30, 60, 90 and 120 minutes post-glucose load (2 g/kg, PO) for assay of whole blood glucose. Animals were terminated by $CO_2$ asphyxiation and cervical dislocation. Food consumption and body weight were recorded daily just prior to dark cycle (0600-0700 hr). The area of the blood glucose response curve corresponding to each animal was calculated by the trapezoid method, using each individual baseline blood glucose measurement prior to glucose administration as reference (t=0). The sum of the trapezoidal areas between the 0, 30, 60, 90 and 120-minute time points corresponding to each animal were summed to obtain the area under the curve (AUC).

Statistics

Except where mentioned, all data are presented as Mean±SEM. Statistical analysis was done using Prism for Windows (version 6.07 GraphPad, San Diego, Calif.). As appropriate, one-way ANOVA or one-way ANOVA repeated measures followed by Dunnett's multiple comparisons test were done. Also, two-way ANOVA and two-way repeated measures ANOVA followed by Sidak's multiple comparison test were performed where different groups were studied over time.

Results

Age Related Changes in Glucose Homeostasis

Figure 12A:
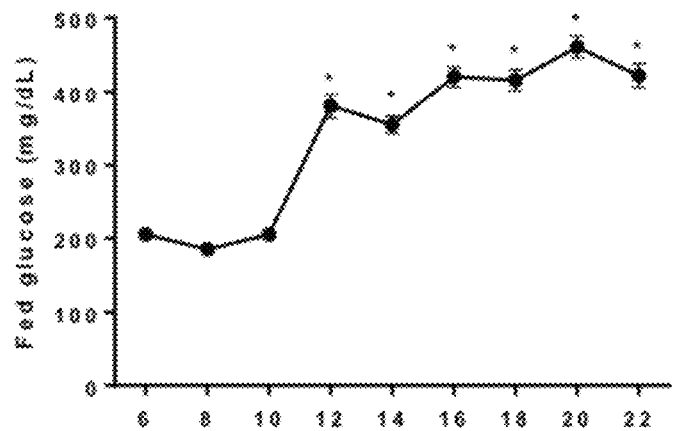
FIGS. 12A and 12B show Post-prandial glucose (FIG. 12A) and insulin (FIG. 12B) concentrations in untreated male FATZO mice (6-22 weeks of age). Hyperglycemia developed spontaneously and was evident in animals as young as 6 weeks of age (FIG. 12A). Insulin responses to developing hyperglycemia create hyperinsulinemia during a period of marked insulin resistance (FIG. 12B). Each value represents the Mean±SEM, n=72. Analysis demonstrated increased glucose concentrations from baseline from 12-22 weeks of age and increases from baseline insulin concentrations from 8-22 weeks, (one-way repeated measures ANOVA, *p<.05 compared to baseline).
Figure 12B:
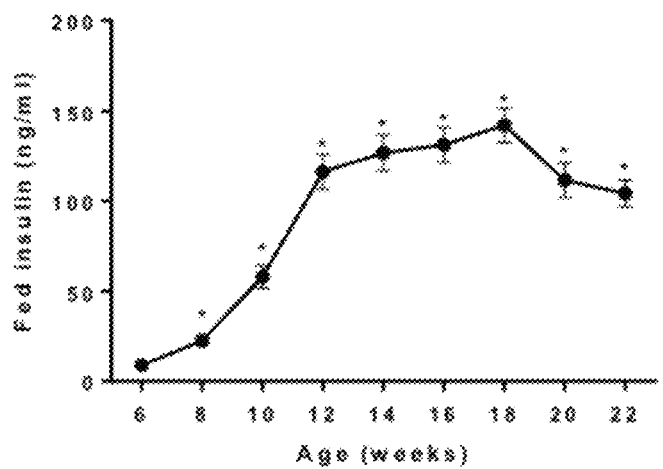

Serum glucose concentrations were determined in a cohort (n=72) of FATZO mice every 2 weeks. Samples were obtained from conscious animals in the fed state. Hyperglycemia developed spontaneously and progressed quickly in FATZO mice when fed standard rodent chow. Serum glucose remained steady from 6-10 weeks of age (≈210 mg/dL), before a rapid increase to 380.4±16.6 mg/dl was noted at 12 weeks. Glucose concentrations then increased more slowly and plateaued at ≅420 mg/dL as animals aged to 22 weeks (FIG. 11A). Serum insulin concentrations were significantly higher in 6-week old FATZO animals compared to literature values for normal mice (9.15±1.5 ng/ml vs. ≅0.5 to 1.5 ng/ml) (FIG. 11B). Concurrent with the progressively increasing glucose concentrations, insulin concentrations rose six-fold to 57.9±6.1 ng/ml in 10-week old animals and fifteen-fold to 142.0±9.7 ng/ml in 18-week old animals. When glucose concentrations were in the mid-400 mg/dL range after 18 weeks of age, insulin concentrations began to fall (FIGS. 12A and 12B).

Comparison to Age-Matched Control Mice

A small cohort of FATZO mice was compared to control C57BL/6J mice (n=6 each) from 6-18 weeks of age. Compared to control mice, FATZO mice develop hyperglycemia, hyperinsulinemia and hypertriglyceridemia spontaneously when fed a standard rodent chow. Insulin resistance, as shown by abnormal glucose disposal, was apparent as early as 6 weeks of age and was concurrent with the accumulation of excess whole body fat.

Figure 13A:
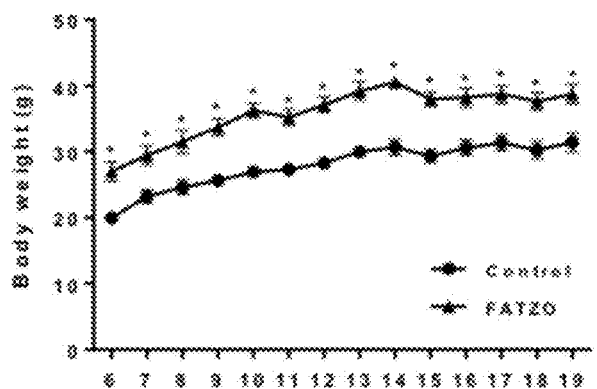
FIGS. 13A-13C show body weight, body fat and serum triglycerides in untreated male FATZO mice compared to control mice. FATZO mice (▲) were significantly heavier (FIG. 13A) compared to age-matched C57BL/6J control mice (●) at each age (Mean±SD). Increased levels of body fat contributes to increased body weight in FATZO mice (FIG. 13B). Body fat in FATZO mice (▲) was significantly higher when compared to control mice (●) from 6-18 weeks of age. Post-prandial serum triglycerides increased in untreated male FATZO mice (▲) as they aged and were significantly elevated when compared to control (●) mice at 10 and 14 weeks of age (n=6, two-way repeated measures (FIGS. 13A, 13B) or two-way ordinary ANOVA (FIG. 13C), *p<.05 when compared to control).
Figure 13B:
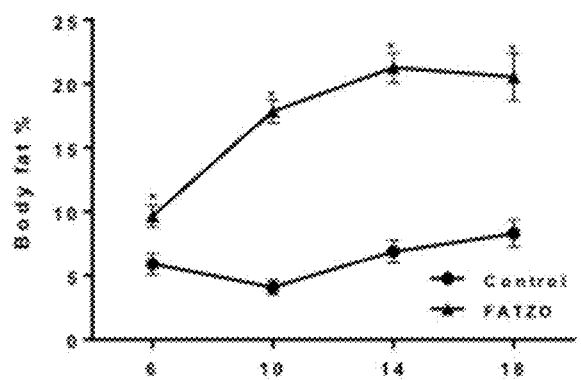
Figure 13C:
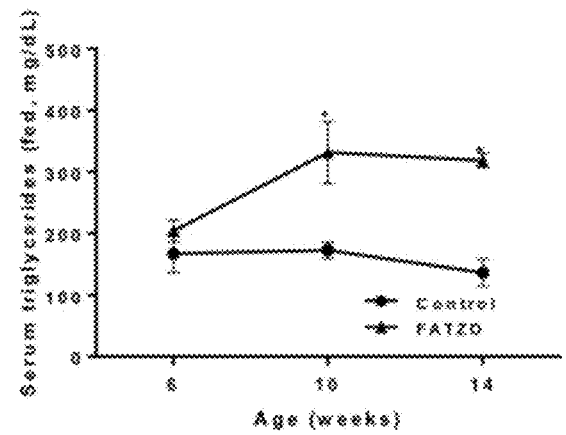

When fed a standard rodent chow, FATZO mice were significantly heavier compared to age matched control mice throughout the study. Six-week-old FATZO mice weighed 27.0±0.6 g at baseline and gained weight steadily, reaching 38.8±0.6 g at 19 weeks of age. Six-week-old control mice weighed 20.0±0.6 g and grew to 31.4±0.6 g by study end (FIG. 13A). The body composition of FATZO mice was also significantly different compared to control mice from 6-18 weeks of age. A higher percentage of body fat was noted in 6-week old FATZO mice compared to control mice (9.7±0.9 vs. 5.9±0.8%, p<.05) and at 18 weeks (20.6±1.8 vs. 8.3±1.0%, p<.05) (FIG. 13B). Feed intake (cumulative) over the course of the study was not significantly different between these groups of animals (310.0±23.0 g for C57BL/6J vs. 330.0±5.6 for FATZO). Serum triglycerides (fed) remained steady in control mice from 6-14 weeks of age, ranging from 167.8±31.1 to 137.0±21.9 mg/dL. Serum triglycerides in FATZO mice were slightly higher although not significantly different compared to control mice at 6 weeks of age (202.6±21.2 vs. 167.8±31.4 mg/dL). Triglycerides were significantly higher in FATZO mice at 10 weeks (331.3±50.6 vs. 173.3±12.9 mg/dL, p<.05) and 14 weeks of age (318.2±11.6 vs. 137.0±21.9 mg/dL, p<.05) (FIG. 13C).

Figure 14A:
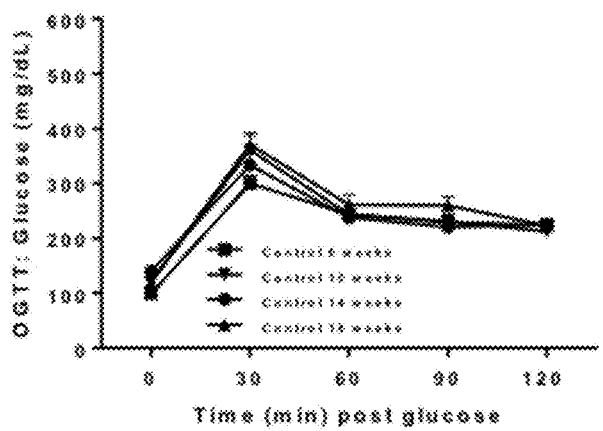
FIGS. 14A-14C show glucose responses to a glucose load during performance of oral glucose tolerance test (OGTT) in control (FIG. 14A), FATZO mice (FIG. 14B) and the areas under the curve for both groups (C). An age-dependent impairment in glucose handling was apparent in FATZO mice compared to control mice in mice as young as 6 weeks. Glucose AUC (FIG. 14C) increased with age in FATZO mice (▲) compared to control mice (●) (two-way repeated measures, ANOVA *p<.05 when compared to control).
Figure 14B:
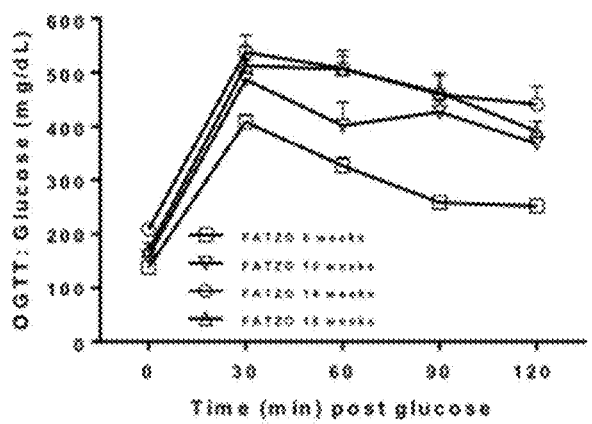
Figure 14C:
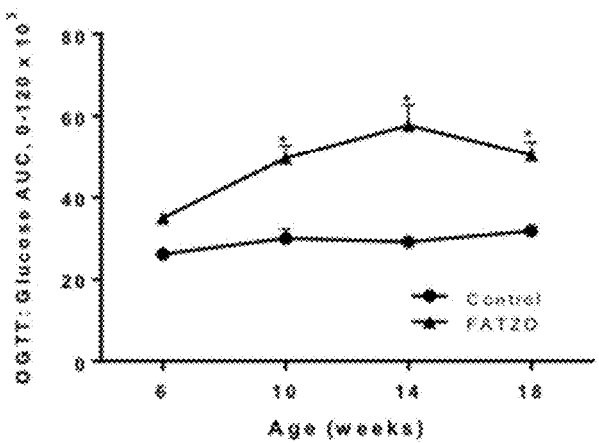

Oral glucose tolerance tests (OGTT) performed monthly on control mice indicated relatively stable disposal of the glucose load from 6-18 weeks of age (FIG. 14A). In contrast, abnormal glucose disposal was prominent in FATZO mice as early as 6 weeks of age. The ability to handle the glucose load deteriorated with age in FATZO mice (FIG. 14B). When represented as the area under the curve, the glucose AUC following a glucose load was not significantly higher in FATZO mice at 6 weeks but did reach significance when compared to control mice at 10, 14 and 18 weeks (FIG. 14C).

Effect of Rosiglitazone and Metformin

In a parallel study, we examined the effect of, rosiglitazone and metformin, on metabolic disturbances in the FATZO mouse model of type 2 diabetes/metabolic syndrome.

Body weight in ten-week old FATZO mice averaged 36.0±0.4 g at study start.

Administration of rosiglitazone 10 mg/kg/day elicited a significant increase in body weight compared to vehicle treated animals over the 8-week observation period (1.8±0.2 vs. 5.3±0.7 g, p<.05). In contrast, metformin treatment resulted in a slight although significant loss of body weight compared to vehicle treated animals (1.8±0.2 vs. -0.2±0.6 g, p<.05).

Serum glucose concentrations in the fed state were 315.6±35.4 mg/dL in animals administered vehicle for 8 weeks. Serum glucose concentrations were somewhat lower compared to vehicle following treatment with rosiglitazone but did not reach statistical significance (315.6±35.4 vs. 233.3±7.7 mg/dL) and significantly reduced with metformin (315.6±35.4 vs. 250.0±12.8 mg/dL, p<.05).

Figure 15A:
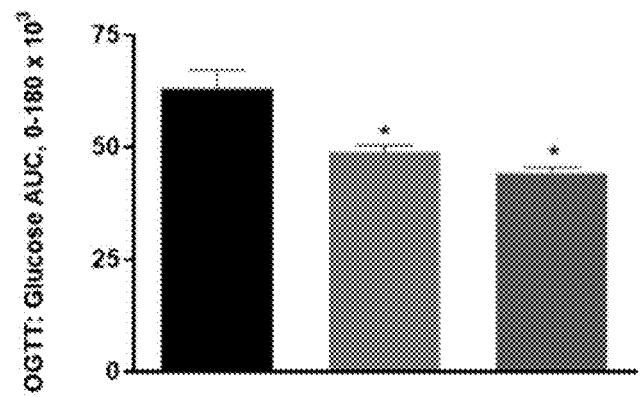
FIGS. 15A-15C show area under the curve (AUC) analysis of glucose (FIG. 15A) and insulin (FIG. 15B) responses during OGTT and calculated insulin sensitivity index (FIG. 15C) (ISI) in FATZO mice following an 8-week administration of rosiglitazone or metformin. Both insulin sensitizers elicited significant reductions in the AUC for glucose in FATZO mice (FIG. 15A). Although it is reduced, insulin AUC did not reach significance for the rosiglitazone group but it did for the metformin group (FIG. 15B). Significant improvement in ISI was also demonstrated with metformin treatment and, although improved, rosiglitazone treatment did not reach statistical significance when compared to vehicle (one-way ANOVA, *p<.05 when compared to vehicle).
Figure 15B:
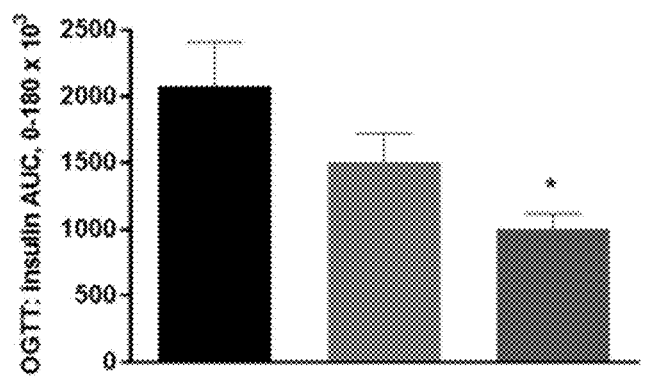
Figure 15C:
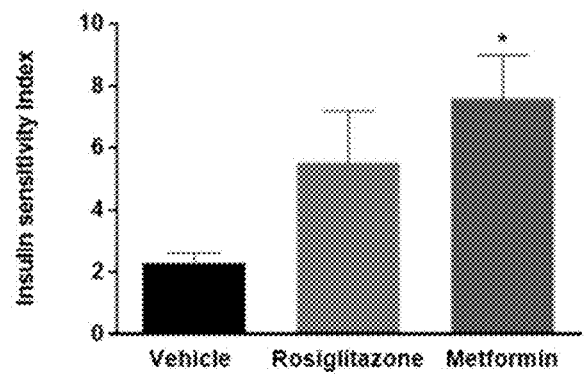

The area under the curve (AUC) for glucose (FIG. 15A) was reduced significantly compared to vehicle following administration of both compounds for 8 weeks. However, only metformin elicited significant improvements in insulin AUC and in the calculated insulin sensitivity index (ISI) (FIGS. 15B and 15C).

Effect of GLP-1 Receptor Agonist Semaglutide

Figure 16A:
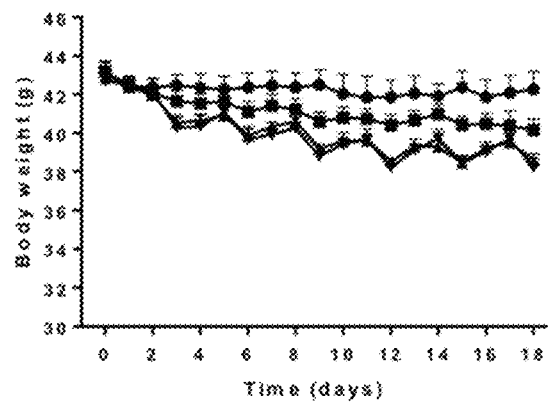
FIGS. 16A-16D show body weight food intake in male FATZO mice during administration of semaglutide (1-10 nmol/kg, SQ, q3d, ×16 days). Semaglutide elicited dose-dependent decreases in body weight compared to vehicle within 2 days of start of treatment (FIG. 16A). At study end, animals administered semaglutide lost significantly more body weight compared to baseline values than vehicle treated animals (FIG. 16B). Daily variation in feed intake was apparent in all groups (FIG. 16C). A transient, dose-dependent reduction in feed intake compared to pre-dose values was observed during the 24 hrs following each semaglutide administration (FIG. 16D). Of note, a boiler failure resulted in decreased humidity of about 25% for one day which correlated with a transient increase in feed intake between day 2 and 3 [Vehicle ●, 1 nmol/kg ■, 3 nmol/kg ▲, and 10 nmol/kg ▼] (one-way ANOVA, *p<.05 when compared to vehicle).
Figure 16B:
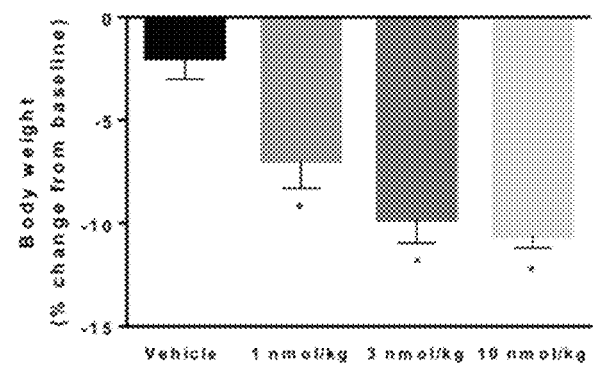

Body weight in FATZO mice at baseline (15-16 weeks of age) averaged 43.0±0.2 g and there was no difference among treatment groups at baseline (43.1±0.5, 43.2±0.5, 42.9±0.5 and 42.7±0.5 g for vehicle, and semaglutide at 1, 3 and 10 nmol/kg, respectively). Body weight in vehicle treated animals remained relatively steady throughout the study, losing 1.9±1.1% of body weight compared to baseline following 16 days of vehicle administration. In contrast, dose-dependent and progressive loss of body weight was noted in semaglutide treated animals. Over the course of the study, a dose-dependent reduction in body weight compared to baseline was observed following semaglutide at 1, 3 and 10 nmol/kg (7.0±1.3, 9.9±1.4 and 10.6±0.6% for the 1, 3 and 10 nmol/kg dose, respectively). This weight loss was significant compared to vehicle for all doses administered (FIGS. 16A and 16B).

Figure 16C:
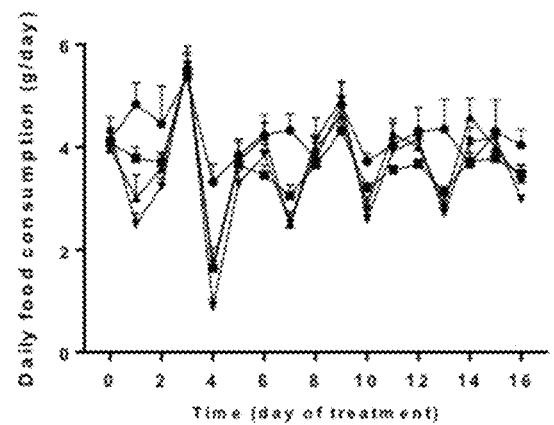
Figure 16D:
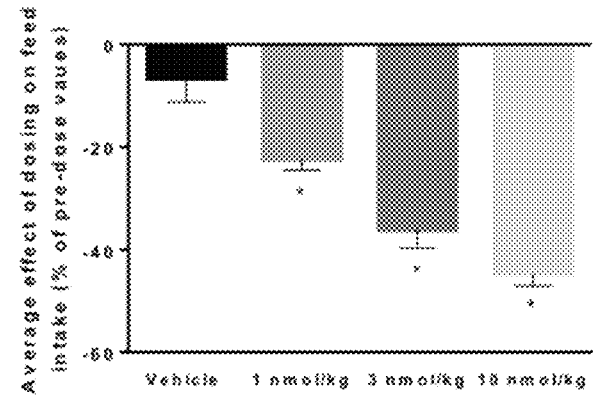

Baseline feed intake averaged 4.1±0.09 g/day for the 6 days prior to study start. Food consumption in semaglutide treated animals was significantly reduced compared to vehicle for the 24 hours following each drug administration (day 1, 4, 7, 10, 13, and 16). Averaged over the six drug administrations, the effect of semaglutide on food consumption (% reduction in food intake compared to pre-dose values) was significantly greater when compared to vehicle (-6.7±4.6%) in all semaglutide groups (-22.4±2.2, -36.1±3.5 and -44.7±2.5% for semaglutide at 1, 3 and 10 nmol/kg, respectively). These effects were transient as food consumption recovered to pre-dose values prior to next dose (FIGS. 16C and 16D).

Figure 17A:
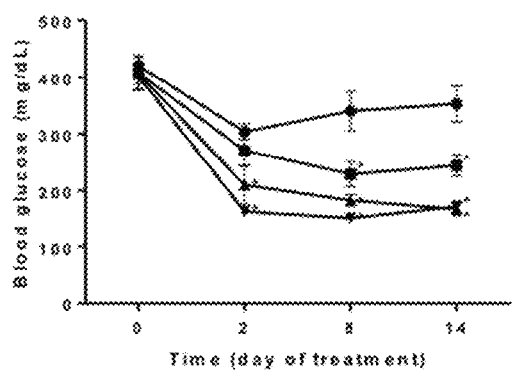
FIGS. 17A-17D show changes in blood glucose and glucose responses to a glucose load during performance of oral glucose tolerance test in male FATZO mice following administration of semaglutide. Post-prandial glucose measured 24 hours after administration of semaglutide was dose-dependently reduced compared to vehicle over the course of the study (FIG. 17A) (two-way ANOVA, *p<.05 when compared to baseline). Terminal glucose data were also plotted as % decrease in glucose concentrations compared to baseline. The responses of all of the semaglutide groups were significantly higher than that of vehicle treated animals (FIG. 17B). Improvements in glucose handling were dose-dependent and significant compared to vehicle when administered at 10 nmol/kg (FIGS. 17C, 17D) [Vehicle ●, 1 nmol/kg ■, 3 nmol/kg ▲, and 10 nmol/kg ▼] (one-way ANOVA, *p<.05 when compared to vehicle).
Figure 17B:
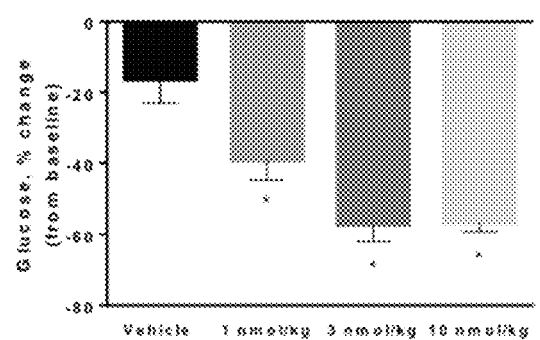

Baseline blood glucose averaged 408.9±11.0 mg/dL in animals selected for study. Fed blood glucose measured twenty-four hours after the first, third and fifth dose was significantly reduced in semaglutide treated animals compared to those administered vehicle except for the 1 nmol/kg group after the first dose. Following the fifth administration, glucose values were reduced compared to baseline by 16.3±6.8, 39.4±5.3, 57.3±4.8 and 56.6±2.5% for vehicle, and semaglutide at 1, 3 and 10 nmol/kg, respectively (FIGS. 17A and 17B).

Figure 17C:
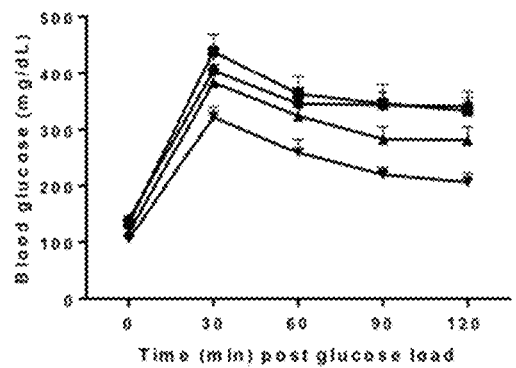
Figure 17D:
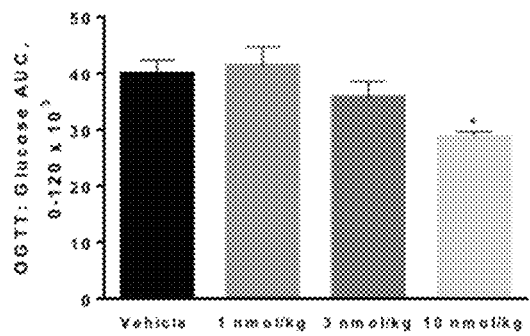

Administration of semaglutide elicited an improvement in glucose disposal. A dose-dependent reduction in the glucose AUC following an oral glucose tolerance test (OGTT) was observed following administration of semaglutide (FIGS. 17A and 17B). A reduction compared to vehicle (−11%) was observed following administration of semaglutide (3.0 nmol/kg); however, this response did not reach significance. The reduction in AUC was significant compared to vehicle for the 10 nmol/kg dose (40.04±2.4, 41.5±3.4, 35.7±2.8 and 28.7±1.0 AUC for vehicle and semaglutide at 1, 3 and 10 nmol/kg, respectively) (FIGS. 17C and 17D).

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A method for producing a non-human animal model of non-alcoholic steatohepatitis (NASH), the method comprising
   (a) obtaining a mouse of six to twelve weeks old, wherein the mouse is generated by crossing C57BL/6 strain and AKR/J strain and inbreeding for at least 30 generations; and
   (b) raising the mouse in a laboratory or facility with a formulated diet of high-fat and high fructose for a period of time sufficient to induce the NASH in the mouse, wherein the formulated diet comprises fat of at least 40% kcal and 5% fructose in drinking water.

2. The method of claim 1, wherein the the non-human animal model has cirrhosis or liver cancer.

3. The method of claim 1, wherein the mouse is about 8 weeks old.

4. The method of claim 1, wherein the period of time is 4 weeks, 16 weeks or 20 weeks.

5. The method of claim 1, wherein the formulated diet comprises protein of about 20% in weight and carbohydrate of about 50% in weight.

6. The method of claim 1, wherein the non-human animal model has type 2 diabetes.

7. The method of claim 1, wherein the non-human animal model has obesity.

8. The method of claim 1, wherein the mouse is raised at 25° C.

* * * * *